(12) United States Patent
Roock et al.

(10) Patent No.: US 9,271,821 B2
(45) Date of Patent: Mar. 1, 2016

(54) ELONGATED TISSUE MATRICES

(71) Applicants: Timothy Roock, Bordentown, NJ (US); Nathaniel Bachrach, Clifton, NJ (US); Benjamin T. Kibalo, Columbia, MD (US)

(72) Inventors: Timothy Roock, Bordentown, NJ (US); Nathaniel Bachrach, Clifton, NJ (US); Benjamin T. Kibalo, Columbia, MD (US)

(73) Assignee: LifeCell Corporation, Branchburg, NJ (US)

( * ) Notice: Subject to any disclaimer, the term of this patent is extended or adjusted under 35 U.S.C. 154(b) by 334 days.

(21) Appl. No.: 13/743,962

(22) Filed: Jan. 17, 2013

(65) Prior Publication Data

US 2013/0190893 A1 Jul. 25, 2013

Related U.S. Application Data

(60) Provisional application No. 61/590,035, filed on Jan. 24, 2012.

(51) Int. Cl.
| | |
|---|---|
| *A61F 2/02* | (2006.01) |
| *A61L 27/36* | (2006.01) |
| *A61L 27/38* | (2006.01) |
| *A61L 27/50* | (2006.01) |
| *A61L 27/54* | (2006.01) |

(52) U.S. Cl.
CPC .............. *A61F 2/02* (2013.01); *A61L 27/3604* (2013.01); *A61L 27/3683* (2013.01); *A61L 27/38* (2013.01); *A61L 27/50* (2013.01); *A61L 27/54* (2013.01); *A61L 2400/06* (2013.01); *A61L 2430/04* (2013.01); *A61L 2430/40* (2013.01)

(58) Field of Classification Search
CPC ... A61F 2/02; A61L 27/3604; A61L 27/3608; A61L 27/3612; A61L 27/362; A61L 27/3625; A61L 27/3629; A61L 27/3633; A61L 27/3641; A61L 27/3683; A61L 27/3695; A61L 27/38; A61L 27/50; A61L 27/54; A61L 2430/00; A61L 2430/04; A61L 2430/40; A61L 2400/06

See application file for complete search history.

(56) References Cited

U.S. PATENT DOCUMENTS

| | | | |
|---|---|---|---|
| 4,347,841 | A | 9/1982 | Benyó et al. |
| 4,350,629 | A | 9/1982 | Yannas et al. |
| 4,352,883 | A | 10/1982 | Lim |
| 4,582,640 | A | 4/1986 | Smestad et al. |
| 4,776,173 | A | 10/1988 | Kamarei et al. |

(Continued)

FOREIGN PATENT DOCUMENTS

| | | |
|---|---|---|
| CA | 1336812 C | 8/1995 |
| FR | 1522286 | 3/1968 |

(Continued)

OTHER PUBLICATIONS

Ahn et al., "The past, present, and future of xenotransplantation" *Yonsei Med J.*, 45(6):1017-1024 (Dec. 31, 2004).

(Continued)

*Primary Examiner* — Ryan Severson
(74) *Attorney, Agent, or Firm* — McCarter & English, LLP; Matthew R. Van Eman

(57) ABSTRACT

Elongated and high aspect ratio tissue treatment products are provided. Methods of making and using the tissue treatment products are also provided. The tissue treatment products can be used as implants that conform to the site of implantation and resist migration away from their implantation site in vivo.

27 Claims, 25 Drawing Sheets

(56) References Cited

U.S. PATENT DOCUMENTS

| | | | |
|---|---|---|---|
| 4,796,603 A | 1/1989 | Dahlke et al. | |
| 4,854,316 A | 8/1989 | Davis | |
| 4,902,508 A | 2/1990 | Badylak et al. | |
| 4,969,912 A | 11/1990 | Kelman et al. | |
| 5,104,957 A | 4/1992 | Kelman et al. | |
| 5,131,850 A | 7/1992 | Brockbank | |
| 5,160,313 A | 11/1992 | Carpenter et al. | |
| 5,231,169 A | 7/1993 | Constantz et al. | |
| 5,254,133 A | 10/1993 | Seid | |
| 5,256,140 A | 10/1993 | Fallick | |
| 5,275,826 A | 1/1994 | Badylak et al. | |
| 5,284,655 A | 2/1994 | Bogdansky et al. | |
| 5,332,802 A | 7/1994 | Kelman et al. | |
| 5,332,804 A | 7/1994 | Florkiewicz et al. | |
| 5,336,616 A | 8/1994 | Livesey et al. | |
| 5,364,756 A | 11/1994 | Livesey et al. | |
| 5,439,684 A | 8/1995 | Prewett et al. | |
| 5,489,304 A | 2/1996 | Orgill et al. | |
| 5,613,982 A | 3/1997 | Goldstein | |
| 5,632,778 A | 5/1997 | Goldstein | |
| 5,634,931 A | 6/1997 | Kugel | |
| 5,641,518 A | 6/1997 | Badylak et al. | |
| 5,648,330 A | 7/1997 | Pierschbacher et al. | |
| 5,695,998 A | 12/1997 | Badylak et al. | |
| 5,712,252 A | 1/1998 | Smith | |
| 5,716,404 A * | 2/1998 | Vacanti et al. | 623/8 |
| 5,716,981 A * | 2/1998 | Hunter et al. | 514/449 |
| 5,728,752 A | 3/1998 | Scopelianos et al. | |
| 5,739,176 A | 4/1998 | Dunn et al. | |
| 5,780,295 A | 7/1998 | Livesey et al. | |
| 5,800,537 A | 9/1998 | Bell | |
| 5,886,026 A * | 3/1999 | Hunter et al. | 514/449 |
| 5,893,888 A | 4/1999 | Bell | |
| 5,942,496 A | 8/1999 | Bonadio et al. | |
| 5,961,552 A * | 10/1999 | Iversen et al. | 623/8 |
| 5,972,007 A | 10/1999 | Sheffield et al. | |
| 5,993,844 A | 11/1999 | Abraham et al. | |
| 5,994,341 A * | 11/1999 | Hunter et al. | 514/449 |
| 6,027,743 A | 2/2000 | Khouri et al. | |
| 6,096,347 A | 8/2000 | Geddes et al. | |
| 6,113,623 A | 9/2000 | Sgro | |
| 6,166,288 A | 12/2000 | Diamond et al. | |
| 6,174,320 B1 | 1/2001 | Kugel et al. | |
| 6,179,872 B1 | 1/2001 | Bell et al. | |
| 6,194,136 B1 | 2/2001 | Livesey et al. | |
| 6,197,036 B1 | 3/2001 | Tripp et al. | |
| 6,214,045 B1 * | 4/2001 | Corbitt et al. | 623/8 |
| 6,231,608 B1 | 5/2001 | Stone | |
| 6,258,125 B1 | 7/2001 | Paul et al. | |
| 6,326,018 B1 | 12/2001 | Gertzman et al. | |
| 6,371,992 B1 | 4/2002 | Tanagho et al. | |
| 6,381,026 B1 | 4/2002 | Schiff et al. | |
| 6,432,710 B1 | 8/2002 | Boss, Jr. et al. | |
| 6,485,723 B1 | 11/2002 | Badylak et al. | |
| 6,554,863 B2 | 4/2003 | Paul et al. | |
| 6,576,265 B1 | 6/2003 | Spievack | |
| 6,599,318 B1 | 7/2003 | Gabbay | |
| 6,610,006 B1 | 8/2003 | Amid et al. | |
| 6,638,284 B1 | 10/2003 | Rousseau et al. | |
| 6,638,308 B2 * | 10/2003 | Corbitt et al. | 623/8 |
| 6,652,593 B2 | 11/2003 | Boyer, II et al. | |
| 6,666,892 B2 | 12/2003 | Hiles et al. | |
| 6,726,660 B2 | 4/2004 | Hessel et al. | |
| 6,767,369 B2 | 7/2004 | Boyer, II et al. | |
| 6,776,800 B2 | 8/2004 | Boyer, II et al. | |
| 6,790,213 B2 | 9/2004 | Cherok et al. | |
| 6,833,408 B2 | 12/2004 | Sehl et al. | |
| 6,881,226 B2 * | 4/2005 | Corbitt et al. | 623/8 |
| 6,933,326 B1 | 8/2005 | Griffey et al. | |
| 7,087,089 B2 * | 8/2006 | Patel et al. | 623/23.72 |
| 7,105,001 B2 | 9/2006 | Mandelbaum | |
| 7,235,295 B2 | 6/2007 | Laurencin et al. | |
| 7,358,284 B2 | 4/2008 | Griffey et al. | |
| 7,425,322 B2 | 9/2008 | Cohn et al. | |
| 7,498,040 B2 | 3/2009 | Masinaei et al. | |
| 7,498,041 B2 | 3/2009 | Masinaei et al. | |
| 7,531,503 B2 * | 5/2009 | Atala et al. | 514/1.1 |
| 7,563,223 B2 * | 7/2009 | Sampson | 600/3 |
| 7,637,948 B2 * | 12/2009 | Corbitt, Jr. | 623/8 |
| 7,668,582 B2 * | 2/2010 | Sirimanne et al. | 600/414 |
| 7,745,217 B2 * | 6/2010 | Patel et al. | 435/378 |
| 7,799,767 B2 | 9/2010 | Lamberti et al. | |
| 7,815,561 B2 | 10/2010 | Forman et al. | |
| 7,838,021 B2 | 11/2010 | Lafont et al. | |
| 7,871,438 B2 * | 1/2011 | Corbitt, Jr. | 623/8 |
| 7,951,880 B2 * | 5/2011 | Lim et al. | 526/72 |
| 7,968,110 B2 * | 6/2011 | Hubbard | 424/423 |
| 8,067,027 B2 * | 11/2011 | Hubbard | 424/425 |
| 8,067,149 B2 | 11/2011 | Livesey et al. | |
| 8,137,688 B2 * | 3/2012 | Zahos et al. | 424/423 |
| 8,157,862 B2 * | 4/2012 | Corbitt, Jr. | 623/7 |
| 8,306,602 B2 * | 11/2012 | Sirimanne et al. | 600/414 |
| 8,320,993 B2 * | 11/2012 | Sirimanne et al. | 600/431 |
| 8,320,994 B2 * | 11/2012 | Sirimanne et al. | 600/431 |
| 8,323,352 B2 | 12/2012 | Friedman et al. | |
| 8,324,449 B2 | 12/2012 | McQuillan et al. | |
| 8,333,803 B2 | 12/2012 | Park et al. | |
| 8,501,645 B2 * | 8/2013 | Pham | 442/339 |
| 8,600,481 B2 * | 12/2013 | Sirimanne et al. | 600/431 |
| 8,668,737 B2 * | 3/2014 | Corbitt, Jr. | 623/7 |
| 2001/0041936 A1 * | 11/2001 | Corbitt et al. | 623/8 |
| 2002/0055143 A1 | 5/2002 | Bell et al. | |
| 2002/0061328 A1 | 5/2002 | Gertzman et al. | |
| 2002/0082697 A1 | 6/2002 | Damien | |
| 2002/0099344 A1 | 7/2002 | Hessel et al. | |
| 2002/0103542 A1 | 8/2002 | Bilbo | |
| 2002/0120347 A1 | 8/2002 | Boyer II et al. | |
| 2002/0165265 A1 * | 11/2002 | Hunter et al. | 514/449 |
| 2002/0197242 A1 | 12/2002 | Gertzman et al. | |
| 2003/0009235 A1 | 1/2003 | Manrique et al. | |
| 2003/0014126 A1 * | 1/2003 | Patel et al. | 623/23.72 |
| 2003/0035843 A1 | 2/2003 | Livesey et al. | |
| 2003/0039678 A1 | 2/2003 | Stone et al. | |
| 2003/0143207 A1 | 7/2003 | Livesey et al. | |
| 2003/0225355 A1 * | 12/2003 | Butler | 602/48 |
| 2004/0037735 A1 | 2/2004 | DePaula et al. | |
| 2004/0049269 A1 * | 3/2004 | Corbitt et al. | 623/8 |
| 2004/0059364 A1 | 3/2004 | Gaskins et al. | |
| 2004/0078077 A1 | 4/2004 | Binette et al. | |
| 2004/0078089 A1 | 4/2004 | Ellis et al. | |
| 2004/0185021 A1 * | 9/2004 | Hubbard | 424/70.13 |
| 2005/0008672 A1 | 1/2005 | Winterbottom et al. | |
| 2005/0009178 A1 | 1/2005 | Yost et al. | |
| 2005/0013870 A1 * | 1/2005 | Freyman et al. | 424/520 |
| 2005/0028228 A1 | 2/2005 | McQuillan et al. | |
| 2005/0043716 A1 | 2/2005 | Frimer | |
| 2005/0054771 A1 | 3/2005 | Sehl et al. | |
| 2005/0058629 A1 | 3/2005 | Harmon et al. | |
| 2005/0080338 A1 * | 4/2005 | Sirimanne et al. | 600/431 |
| 2005/0118230 A1 | 6/2005 | Hill et al. | |
| 2005/0142161 A1 * | 6/2005 | Freeman et al. | 424/423 |
| 2005/0159822 A1 | 7/2005 | Griffey et al. | |
| 2005/0181016 A1 * | 8/2005 | Freyman et al. | 424/426 |
| 2005/0187624 A1 * | 8/2005 | Corbitt, Jr. | 623/8 |
| 2005/0240073 A1 * | 10/2005 | Apffelstaedt et al. | 600/2 |
| 2005/0288691 A1 | 12/2005 | Leiboff | |
| 2006/0036159 A1 * | 2/2006 | Sirimanne et al. | 600/414 |
| 2006/0073592 A1 | 4/2006 | Sun et al. | |
| 2006/0105026 A1 | 5/2006 | Fortune et al. | |
| 2006/0106419 A1 | 5/2006 | Gingras | |
| 2006/0115515 A1 | 6/2006 | Pirhonen et al. | |
| 2006/0204441 A1 * | 9/2006 | Atala et al. | 424/9.6 |
| 2006/0210960 A1 | 9/2006 | Livesey et al. | |
| 2006/0247206 A1 | 11/2006 | Feins | |
| 2006/0264399 A1 * | 11/2006 | Lim et al. | 514/54 |
| 2006/0276908 A1 | 12/2006 | Sogaard-Anderson et al. | |
| 2006/0282164 A1 * | 12/2006 | Seastrom | 623/8 |
| 2007/0003759 A1 * | 1/2007 | Pham | 428/364 |
| 2007/0009586 A1 | 1/2007 | Cohen et al. | |
| 2007/0009888 A1 * | 1/2007 | Macina | 435/6 |
| 2007/0028932 A1 * | 2/2007 | Sampson | 128/898 |
| 2007/0037283 A1 * | 2/2007 | Patel et al. | 435/380 |
| 2007/0078522 A2 | 4/2007 | Griffey et al. | |
| 2007/0104692 A1 * | 5/2007 | Quijano et al. | 424/93.7 |

(56) References Cited

U.S. PATENT DOCUMENTS

| | | | |
|---|---|---|---|
| 2007/0104693 A1* | 5/2007 | Quijano et al. | 424/93.7 |
| 2007/0104694 A1* | 5/2007 | Quijano et al. | 424/93.7 |
| 2007/0104695 A1* | 5/2007 | Quijano et al. | 424/93.7 |
| 2007/0104759 A1 | 5/2007 | Dunn et al. | |
| 2007/0111937 A1 | 5/2007 | Pickar et al. | |
| 2007/0202173 A1 | 8/2007 | Cueto-Garcia | |
| 2007/0248575 A1 | 10/2007 | Connor et al. | |
| 2007/0293878 A1 | 12/2007 | Butsch | |
| 2008/0027542 A1 | 1/2008 | McQuillan et al. | |
| 2008/0027562 A1 | 1/2008 | Fujisato et al. | |
| 2008/0033461 A1 | 2/2008 | Koeckerling et al. | |
| 2008/0071300 A1 | 3/2008 | Popadiuk et al. | |
| 2008/0091277 A1 | 4/2008 | Deusch et al. | |
| 2008/0095819 A1 | 4/2008 | Gourdie et al. | |
| 2008/0113035 A1 | 5/2008 | Hunter | |
| 2008/0131509 A1 | 6/2008 | Hossainy et al. | |
| 2008/0147199 A1 | 6/2008 | Yost et al. | |
| 2008/0167729 A1 | 7/2008 | Nelson et al. | |
| 2008/0228164 A1* | 9/2008 | Nicoson et al. | 604/506 |
| 2009/0035289 A1 | 2/2009 | Wagner et al. | |
| 2009/0117188 A1* | 5/2009 | Gershkovich et al. | 424/484 |
| 2009/0130221 A1 | 5/2009 | Bolland et al. | |
| 2009/0138074 A1* | 5/2009 | Freyman et al. | 623/1.38 |
| 2009/0181104 A1* | 7/2009 | Rigotti et al. | 424/574 |
| 2009/0306790 A1 | 12/2009 | Sun | |
| 2009/0312746 A1* | 12/2009 | Khouri | 604/522 |
| 2010/0021961 A1 | 1/2010 | Fujisato et al. | |
| 2010/0040687 A1 | 2/2010 | Pedrozo et al. | |
| 2010/0087839 A1* | 4/2010 | Nielsen et al. | 606/151 |
| 2010/0100179 A1* | 4/2010 | Hubbard | 623/8 |
| 2010/0121445 A1* | 5/2010 | Corbitt, Jr. | 623/8 |
| 2010/0136645 A1* | 6/2010 | Min et al. | 435/173.1 |
| 2010/0209408 A1 | 8/2010 | Livesey et al. | |
| 2010/0249927 A1* | 9/2010 | Yang et al. | 623/11.11 |
| 2010/0272782 A1 | 10/2010 | Owens et al. | |
| 2011/0020271 A1 | 1/2011 | Niklason et al. | |
| 2011/0076920 A1* | 3/2011 | Jackson | 450/57 |
| 2011/0082547 A1* | 4/2011 | Corbitt, Jr. | 623/8 |
| 2011/0151011 A1* | 6/2011 | Flynn | 424/490 |
| 2011/0208302 A1* | 8/2011 | Glicksman | 623/8 |
| 2012/0010728 A1 | 1/2012 | Sun et al. | |
| 2012/0040013 A1 | 2/2012 | Owens et al. | |
| 2012/0179251 A1* | 7/2012 | Corbitt, Jr. | 623/8 |
| 2012/0263763 A1 | 10/2012 | Sun et al. | |
| 2013/0053960 A1 | 2/2013 | Park et al. | |
| 2013/0121970 A1 | 5/2013 | Owens et al. | |
| 2013/0131655 A1* | 5/2013 | Rigotti et al. | 606/8 |
| 2013/0190893 A1* | 7/2013 | Roock et al. | 623/23.72 |
| 2014/0100656 A1* | 4/2014 | Namnoum et al. | 623/8 |
| 2014/0142696 A1* | 5/2014 | Corbitt, Jr. | 623/8 |
| 2014/0257481 A1* | 9/2014 | Brooks et al. | 623/8 |

FOREIGN PATENT DOCUMENTS

| | | |
|---|---|---|
| WO | WO 84/04880 A1 | 12/1984 |
| WO | WO 91/16867 A1 | 11/1991 |
| WO | WO 94/03584 A1 | 2/1994 |
| WO | WO 95/22301 A1 | 8/1995 |
| WO | WO 96/13974 A1 | 5/1996 |
| WO | WO 99/32049 A1 | 7/1999 |
| WO | WO 99/47080 A1 | 9/1999 |
| WO | WO 99/51170 A1 | 10/1999 |
| WO | WO 99/63051 A2 | 12/1999 |
| WO | WO 99/65470 A1 | 12/1999 |
| WO | WO 00/16822 A1 | 3/2000 |
| WO | WO 00/47114 A1 | 8/2000 |
| WO | WO 03/017826 A2 | 3/2003 |
| WO | WO 03/032735 A1 | 4/2003 |
| WO | WO 2005/009134 A1 | 2/2005 |
| WO | WO 2007/043513 A1 | 4/2007 |
| WO | WO 2007/134134 A2 | 11/2007 |
| WO | WO 2009/009620 A2 | 1/2009 |
| WO | WO 2010/019753 A2 | 2/2010 |
| WO | WO 2010/078353 A2 | 7/2010 |
| WO | WO 2012/142419 A1 | 10/2012 |
| WO | WO 2012/166784 A1 | 12/2012 |

OTHER PUBLICATIONS

Allman et al., "Xenogeneic Extracellular Matrix Grafts Elicit a TH2-Restricted Immune Response" *Transplantation*, 71(11):1631-1640 (Jun. 15, 2001).

Aycock et al., "Parastomal Hernia Repair With Acellular Dermal Matrix" *J. Wound Ostomy Continence Nurs.*, 34(5):521-523 (2007).

Badylak et al., "Endothelial cell adherence to small intestinal submucosa: An acellular bioscaffold" *Biomaterials*, 20:2257-2263 (1999).

Badylak et al., "Extracellular Matrix As a Biological Scaffold Material: Structure and Function" *Acta Biomaterialia*, 5(1):1-13 (2009).

Beniker et al., "The use of acellular dermal matrix as a scaffold for periosteum replacement" *Orthopedics*, 26(5 Suppl):s591-s596 (May 2003).

Bruder et al., "The Effect of Implants Loaded with Autologous Mesenchymal Stem Cells on the Healing of Canine Segmental Bone Defects" *J. Bone Joint Surg.*, 80:985-986 (1998).

Buma et al., "Tissue engineering of the meniscus" *Biomaterials*, 25(9):1523-1532 (2004).

Chaplin et al., "Use of an Acellular Dermal Allograft for Dural Replacement: An Experimental Study" *Neurosurgery*, 45(2):320-327 (Aug. 1999).

Chen et al. "Acellular Collagen Matrix As a Possible 'Off the Shelf' Biomaterial for Urethral Repair" *Urology*, 54(3):407-410 (1999).

Collins et al., "Cardiac xenografts between primate species provide evidence for the importance of the α-galactosyl determinant in hyperacute rejection" *J. Immunol.*, 154:5500-5510 (1995).

Costantino et al., "Human Dural Replacement With Acellular Dermis: Clinical Results and a Review of the Literature" *Head & Neck*, 22:765-771 (Dec. 2000).

Dobrin et al., "Elastase, collagenase, and the biaxial elastic properties of dog carotid artery" *Am. J. Physiol. Heart Circ. Physiol.*, 247:H124-H131 (1984).

Edel, "The use of a connective tissue graft for closure over an immediate implant covered with occlusive membrane" *Clin. Oral Implants Res.*, 6:60-65 (1995) (Abstract).

Fowler et al., "Ridge Preservation Utilizing an Acellular Dermal Allograft and Demineralized Freeze-Dried Bone Allograft: Part II. Immediate Endosseous Impact Placement" *J. Periodontol.*, 71:1360-1364 (2000).

Fowler et al., "Root Coverage with an Acellular Dermal Allograft: A Three-Month Case Report" *J. Contemp. Dental Pract.*, 1(3):1-8 (2000).

Galili et al., "Man, Apes, and Old World Monkeys Differ from Other Mammals in the Expression of α-Galactosyl Epitopes on Nucleated Cells" *J. Biol. Chem.*, 263(33):17755-17762 (1988).

Galili et al., "Interaction Between Human Natural Anti-α-Galactosyl Immunoglobulin G and Bacteria of the Human Flora" *Infect. Immun.*, 56(7):1730-1737 (1988).

Galili et al., "Interaction of the Natural Anti-Gal Antibody with α-Galactosyl Epitopes: a Major Obstacle for Xenotransplantation in Humans" *Immunology Today*, 14(10):480-482 (1993).

Gamba et al. "Experimental abdominal wall defect repaired with acellular matrix" *Pediatr. Surg. Int.*, 18:327-331 (2002).

Gazdar et al., "SV40 and human turnours: Myth, association or casualty?" *Nat. Rev. Cancer*, 2(12):957-964 (2002).

Gebhart et al., "A radiographical and biomechanical study of demineralized bone matrix implanted into a bone defect of rat femurs with and without bone marrow" *Acta Orthop. Belg.*, 57(2):130-143 (1991) (Abstract).

Gong et al., "A sandwich model for engineering cartilage with acellular cartilage sheets and chondrocytes" *Biomaterials*, 32:2265-2273 (2011).

Good et al., "Identification of carbohydrate structures that bind human antiporcine antibodies: Implications for discordant xenografting in humans" *Transplant. Proc.*, 24(2):559-562 (Apr. 1992).

(56) References Cited

OTHER PUBLICATIONS

Greenstein et al., "Parastomal Hernia Repair Using Cross-Linked Porcine Dermis: Report of a Case" *Surg. Today*, 38:1048-1051 (2008).
Griffey et al., "Particulate Dermal Matrix as an Injectable Soft Tissue Replacement Material" *J. Biomed. Mater. Res. (Appl. Biomater.)*, 58(1):10-15 (2001).
Hamadeh et al., "Human natural anti-Gal IgG regulates alternative complement pathway activation on bacterial surfaces" *J. Clin. Invest.*, 89:1223-1235 (Apr. 1992).
Hammond et al., "Human in vivo Cellular Response to a Cross-Linked Acellular Collagen Implant" *Br. J. Surg.*, 95:438-446 (2008).
Hammond et al., "Parastomal Hernia Prevention Using a Novel Collagen Implant: A Randomised Controlled Phase 1 Study" *Hernia*, 12:475-481 (2008).
Harris, "A Comparative Study of Root Coverage Obtained with an Acellular Dermal Matrix Versus a Connective Tissue Graft: Results of 107 Recession Defects in 50 Consecutively Treated Patients" *Int. J. Periodontics Restorative Dentist.*, 20(1):51-59 (2000).
Harris, "Root Coverage With a Connective Tissue With Partial Thickness Double Pedicle Graft and an Acellular Dermal Matrix Graft: A Clinical and Histological Evaluation of a Case Report" *J. Periodontol.*, 69:1305-1311 (1998).
Hildebrand et al. "Response of donor and recipient cells after transplantation of cells to the ligament and tendon" *Microsc. Res. Tech.*, 58(1):34-38 (2002).
Inan et al., "Laparoscopic repair of parastomal hernia using a porcine dermal collagen (Permacol™) implant" *Dis Colon Rectum*, 50(9):1465 (Sep. 2007).
International Search Report issued in International Patent Application No. PCT/US99/13861, mailed Oct. 18, 1999 (4 pages).
International Search Report issued in International Patent Application No. PCT/US02/33456, mailed Feb. 20, 2003 (3 pages).
International Search Report and Written Opinion issued in International Patent Application No. PCT/US2009/065087, mailed Aug. 3, 2010 (8 pages).
International Search Report and Written Opinion issued in International Patent Application No. PCT/US2009/046193, mailed Jul. 30, 2010 (12 pages).
International Search Report and Written Opinion issued in International Patent Application No. PCT/US2011/047041, mailed Oct. 25, 2011 (11 pages).
International Search Report and Written Opinion issued in International Patent Application No. PCT/US2012/064103, mailed Feb. 1, 2013 (12 pages).
International Search Report and Written Opinion issued in International Patent Application No. PCT/US2012/070246, mailed Feb. 22, 2013 (11 pages).
International Search Report and Written Opinion issued in International Patent Application No. PCT/US2012/070250, mailed Feb. 22, 2013 (12 pages).
International Search Report and Written Opinion issued in International Patent Application No. PCT/US2013/021909, mailed May 29, 2013 (6 pages).
Karlinsky et al., "In Vitro Effects of Elastase and Collagenase on Mechanical Properties of Hamster Lungs" *Chest*, 69(2 Suppl,):275-276 (1976).
Kay et al., "Guided Bone Regeneration: Integration of a Resorbable Membrane and Bone Graft Material" *Pract. Periodontics Aesthet., Dent.*, 9(2):185-194 (Mar. 1997).
Kilpadi et al., "Evaluation of closed incision management with negative pressure wound therapy (CIM): Hematoma/seroma and involvement of the lymphatic system" *Wound Rep. Reg.*, 19:588-596 (2001).
Kish et al., "Acellular Dermal Matrix (AlloDerm): New Material in the Repair of Stoma Site Hernias" *The American Surgeon*, 71:1047-1050 (Dec. 2005).
Kridel et al., "Septal Perforation Repair with Acellular Human Dermal Allograft" *Arch. Otolaryngol. Head Neck Surg.*, 124:73-78 (Jan. 1998).

Laidlaw et al., "Tympanic Membrane Repair With a Dermal Allograft" *Laryngoscope*, 111:702-707 (Apr. 2001).
Lee et al., "In vitro evaluation of a poly(lactide-co-glycolide)-collagen composite scaffold for bone regeneration" *Biomaterials*, 27:3466-3472 (2006).
Lu et al., "Novel Porous Aortic Elastin and Collagen Scaffolds for Tissue Engineering" *Biomaterials*, 25(22):5227-5237 (2004).
Lynn et al., "Antigenicity and Immunogenicity of Collagen" *J. Biomed. Mater. Res. Part B: Appl. Biomater.*, 71B:343-354 (2004).
Mantovani et al., "Reconstructive urethroplasty using porcine acellular matrix: Preliminary results" *Archivio Italiano di Urologia e Andrologia*, 74(3):127-128 (2002).
Marzaro et al., "Autologous satellite cell seeding improves in vivo biocompatibility of homologous muscle acellular matrix implants" *Int. J. Mol. Med.*, 10:177-182 (2002).
Merguerian et al., "Acellular bladder matrix allografts in the regeneration of functional bladders: Evaluation of large-segment(>24cm$^2$) substitution in a porcine model" *BJU International*, 85:894-898 (2000).
Nielsen et al., "Biodegradable guide for bone regeneration. Polyurethane membranes tested in rabbit radius defects" *Acta Orthop. Scand.*, 63(1):66-69 (1992).
Novaes, Jr. et al., "Acellular Dermal Matrix Graft as a Membrane for Guided Bone Regeneration: A Case Report" *Implant Dentistry*, 10(3):192-196 (2001).
Omae et al., "Multilayer Tendon Slices Seeded with Bone Marrow Stromal Cells: A Novel Composite for Tendon Engineering" *J. Orthop. Res.*, 27:937-942 (Jul. 2009).
Parnigotto et al., "Experimental defect in rabbit urethra repaired with acellular aortic matrix" *Urol. Res.*, 28:46-51 (2000).
Pluchino et al., "Neural stem cells and their use as therapeutic tool in neurological disorders" *Brain Res. Rev.*, 48(2):211-219 (2005).
Qui et al., "Evaluation of Bone Regeneration at Critical-Sized Calvarial Defect by DBM/AM Composite" *J. Biomed. Mater. Res. Part B: Appl. Biomater.*, 81(2):516-523 (2007).
Rabie et al., "Integration of endochondral bone grafts in the presence of demineralized bone matrix" *Int. J. Oral Maxillofac. Surg.*, 25:311-318 (1996)
Reddy et al. "Regeneration of Functional Bladder Substitutes Using Large Segment Acellular Matrix Allografts in a Porcine Model" *J. Urol.*, 164:936-941 (Sep. 2000).
Reihsner et al., "Biomechanical properties of elastase treated palmar aponeuroses" *Connective Tissue Research*, 26:77-86 (1991).
Ruszczak, "Effect of collagen matrices on dermal wound healing" *Adv. Drug Delivery Rev.*, 55:1595-1611(2003).
Sandor et al., "Host response to implanted porcine-derived biological materials in a primate model of abdominal wall repair" *Tissue Engineering: Part A*, 14(12):2021-2031 (2008).
Sandrin et al., "Anti-pig IgM antibodies in human serum react predominantly with Gal(alpha 1-3)Gal epitopes" *Proc. Natl. Acad. Sci. USA*, 90:11391-11395 (1993).
Seandel et al. "Growth factor-induced angiogenesis in vivo requires specific cleavage of fibrillar type I collagen" *Blood*, 97:2323-2332 (Apr. 2001).
Simon et al., "Early failure of the tissue engineered porcine heart valve SYNERGRAFT™ in pediatric patients" *Eur. J. Cardiothorac. Surg.*, 23(6):1002-1006 (2003).
Sodian et al., "Early In Vivo Experience With Tissue-Engineered Trileaflet Heart Valves" *Circulation*, 102(Suppl. III):III22-III29 (2000).
Stanworth et al., "Stem cells: Progress in research and edging towards the clinical setting" *Clin. Med.*, 1(5):378-382 (Sep./Oct. 2001).
Suckow et al., "Enhanced bone regeneration using porcine small intestinal submucosa" *J. Invest. Surg.*, 12(5):277-287 (Sep./Oct. 1999).
Tauro et al., "Comparison of bovine collagen xenografts to autografts in the rabbit" *Clin. Orthop. Relat. Res.*, 266:271-284 (May 1991).
Tedder et al., "Stabilized Collagen Scaffolds for Heart Valve Tissue Engineering" *Tissue Engineering: Part A*, 00(00):1-12 (2008).
U.S. Appl. No. 09/762,174, filed Nov. 22, 2000, by Griffey et al.: Non-Final Office Action, dated Jan. 18, 2002.
U.S. Appl. No. 09/762,174, filed Nov. 22, 2000, by Griffey et al.: Final Office Action, dated Aug. 21, 2002.

(56) References Cited

OTHER PUBLICATIONS

U.S. Appl. No. 09/762,174, filed Nov. 22, 2000, by Griffey et al.: Non-Final Office Action, dated Dec. 30, 2003.
U.S. Appl. No. 09/762,174, filed Nov. 22, 2000, by Griffey et al.: *Ex Parte Quayle* Action, dated Aug. 11, 2004.
U.S. Appl. No. 09/762,174, filed Nov. 22, 2000, by Griffey et al.: Notice of Allowance, dated Jan. 6, 2005.
U.S. Appl. No. 10/273,780, filed Oct. 18, 2002, by Livesey et al.: Non-Final Office Action, dated Oct. 21, 2005.
U.S. Appl. No. 10/273,780, filed Oct. 18, 2002, by Livesey et al.: Non-Final Office Action, dated Jun. 12, 2006.
U.S. Appl. No. 10/273,780, filed Oct. 18, 2002, by Livesey et al.: Final Office Action, dated Mar. 26, 2007.
U.S. Appl. No. 10/273,780, filed Oct. 18, 2002, by Livesey et al.: Non-Final Office Action, dated May 29, 2008.
U.S. Appl. No. 10/273,780, filed Oct. 18, 2002, by Livesey et al.; Final Office Action, dated Jul. 6, 2009.
U.S. Appl. No. 10/273,780, filed Oct. 18, 2002, by Livesey et al.: Non-Final Office Action, dated Dec. 24, 2009.
U.S. Appl. No. 10/273,780, filed Oct. 18, 2002, by Livesey et al.: Final Office Action, dated Jun. 3, 2010.
U.S. Appl. No. 10/273,780, filed Oct. 18, 2002, by Livesey et al.: Appeal Brief, dated Nov. 3, 2010.
U.S. Appl. No. 10/273,780, filed Oct. 18, 2002, by Livesey et al.: Examiner's Answer to Appeal Brief, dated Jan. 26, 2011.
U.S. Appl. No. 10/273,780, filed Octooer 18, 2002, by Livesey et al.: Patent Board of Appeals Decision, dated Sep. 17, 2012.
U.S. Appl. No. 10/273,780, filed Oct. 18, 2002, by Livesey et al.: Non-Final Office Action, dated Dec. 7, 2012.
U.S. Appl. No. 11/040,127, filed Jan. 20, 2005, by Griffey et al.: Non-Final Office Action, dated Oct. 13, 2006.
U.S. Appl. No. 11/040,127, filed Jan. 20, 2005, by Griffey et al.: Non-Final Office Action, dated Apr. 10, 2007.
U.S. Appl. No. 11/040,127, filed Jan. 20, 2005, by Griffey et al.: Notice of Allowance, dated Nov. 21, 2007.
U.S. Appl. No. 12/621,876, filed Nov. 19, 2009, by Friedman et al.: Notice of Allowance, dated Aug. 2, 2012.
U.S. Appl. No. 12/716,828, filed Mar. 3, 2010, by Livesey et al.: Non-Final Office Action, dated Jun. 14, 2010.
U.S. Appl. No. 12/716,828, filed Mar. 3, 2010, by Livesey et al.: Non-Final Office Action, dated Nov. 10, 2010.
U.S. Appl. No. 12/716,828, filed Mar. 3, 2010, by Livesey et al.: Non-Final Office Action, dated Apr. 26, 2013.
U.S. Appl. No. 13/415,355, filed Mar. 8, 2012, by Sun et al.: Non-Final Office Action, dated Aug. 29, 2012.
U.S. Appl. No. 13/415,355, filed Mar. 8, 2012, by Sun et al.: Final Office Action, dated Feb. 27, 2013.
U.S. Appl. No. 13/717,808, filed Dec. 18, 2012, by Hayzlett et al.
U.S. Appl. No. 13/717,828, filed Dec. 18, 2012, by Hayzlett.
U.S. Appl. No. 13/868,588, filed Apr. 23, 2013, by Hayzlett.
Van Nooten et al., "Acellular porcine and kangaroo aortic valve scaffolds show more intense immune-mediated calcification than cross-linked Toronto SPV® valves in the sheep model" *Interact. CardioVasc. Thorac. Surg.*, 5:544-549 (Jul. 2006).
Vunjak-Novakovic et al., "Tissue engineering of ligaments" *Annu. Rev. Biomed. Eng.*, 6:131-156 (2004).
Wagshall et al., "Acellular dermal matrix allograft in the treatment of mucogingival defects in children: Illustrative case report" *J. Dentist. Children*, 69(1):39-43 (Jan.-Apr. 2002).
Warren et al., "Dural Repair Using Acellular Human Dermis: Experience with 200 Cases: Technique Assessment" *Neurosurgery*, 46(6):1391-1396 (Jun. 2000).
Wefer et al., "Homologous acellular matrix graft for vaginal repair in rats: A pilot study for a new reconstructive approach" *World J. Urol.*, 20:260-263 (2002).
Wright Medical Technology, "Comparative Analysis: GraftJacket™ Periosteum Replacement Scaffold & Sis™ Porcine Small Intestinal Submucosa" Medical Brochure (2002) (5 pages).
Wright Medical Technology, "Comparative Analysis: GraftJacket™ Periosteum Replacement Scaffold vs. Fascia Lata" Medical Brochure (2002) (7 pages).
Wright Medical Technology, "GraftJacket™ Acellular Periosteum Replacement Scaffold: An Ideal Template for Rapid Revascularization and Cellular Repopulation" Technical Monograph, SK 836-602 (2002) (11 pages).
Wright Medical Technology, "Preliminary Pre-Clinical Studies on GraftJacket™ Acellular Periosteum Replacement Scaffold" Medical Brochure, SK 898-892 (2002) (10 pages).
Written opinion issued in International Patent Application PCT/US99/13861, mailed May 10, 2000 (5 pages).
Xu et al., "A Porcine-Derived Acellular Dermal Scaffold That Supports Soft Tissue Regeneration: Removal of Terminal Galactose-α-(1,3)-Galactose and Retention of Matrix Structure" *Tissue Engineering: Part A*, 15(00):1-13 (2009).
Yuan et al., "Effects of collagenase and elastase on the mechanical properties of lung tissue strips" *J. App. Physiol.*, 89:3-14 (2000).
Zhao et al., "The Study of the Feasibility of Segmental Bone Defect Repair with Tissue-Engineered Bone Membrane: A Qualitative Observation" *Strat. Traum. Limb Recon,.* 3:57-64 (2008).
Zheng et al. "Porcine small intestine submucosa (SIS) is not an acellular collagenous matrix and contains porcine DNA: Possible implications in human implantation" *J. Biomed. Meter. Res. B: Appl. Biomater.*, 73(1):61-67 (2005).

* cited by examiner

ELONGATED TISSUE MATRICES

This application claims priority to U.S. Provisional Application No. 61/590,035, filed Jan. 24, 2012, which is incorporated herein by reference in its entirety.

The present disclosure relates generally to methods of making and using elongated tissue matrices, and more particularly, to methods of making and using tissue matrices having a high aspect ratio.

Various tissue-derived products are used to repair, regenerate, heal, or otherwise treat diseased or damaged tissues and organs. Such products can include intact tissue grafts and/or partially or completely decellularized tissues. These tissue treatment products generally have a shape that is defined by their tissue of origin. For example, dermal or intestinal products will generally comprise sheets of relatively flexible materials. However, not all wounds, voids, and/or other tissue treatment sites are amenable to treatment with tissue matrices in the form of a sheet. For example, a potential drawback of using sheet material is the inability to fully conform the sheet to the shape of the void, wound, or tissue being treated. Similarly, treatment with injectable materials (e.g. a non-sheet of particulate material delivered via syringe) may also be potentially challenging in cases where the injectable matrix has a tendency to migrate away from the void, wound, or tissue being treated. This migration could be a concern cosmetically and/or physiologically.

In order to treat, repair, heal or regenerate certain tissue or organ defects, it may be desirable to use materials capable of maintaining shapes or configurations that more closely conform to the anatomic structures to be treated and that reduce the rate of migration away from the implant site. Accordingly, disclosed herein are methods of producing elongated acellular tissue matrices that can be used to fill a void, wound, or other space in tissue in need of treatment, repair, healing, or regeneration. The elongated tissue matrices can be molded to fill a desired shape, while also reducing the risk that the implant will migrate away from the implant site. Also disclosed herein are methods of treatment using such matrices.

DESCRIPTION OF CERTAIN EXEMPLARY EMBODIMENTS

Figure 1:
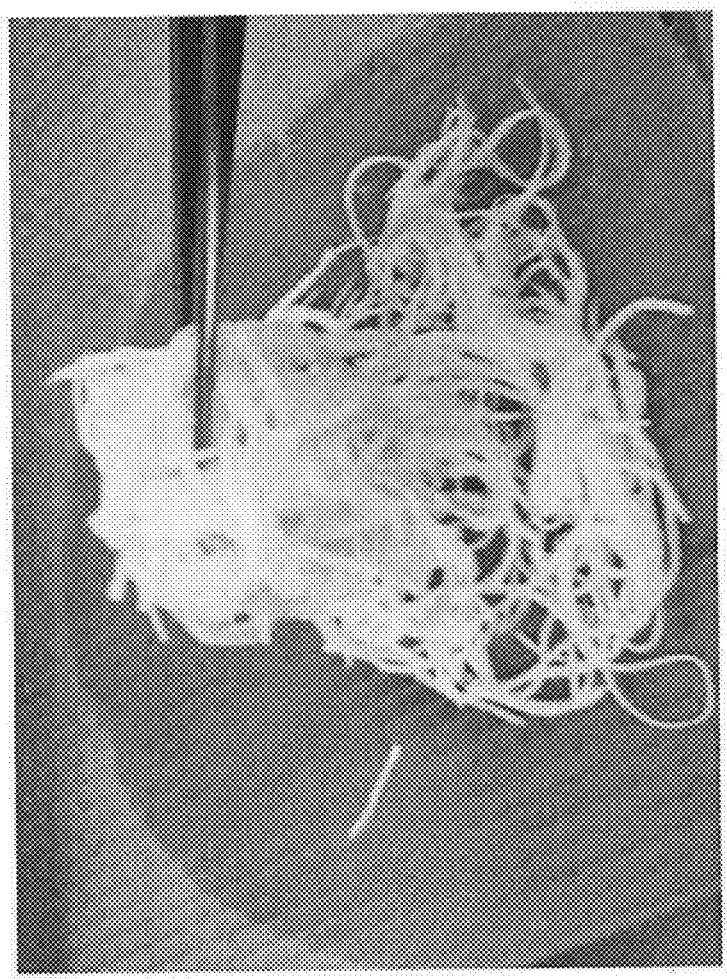
FIG. 1 is a photograph of an acellular tissue treatment product according to certain embodiments of the present disclosure.

Reference will now be made in detail to certain exemplary embodiments according to the present disclosure, certain examples of which are illustrated in the accompanying drawings.

Disclosed herein are tissue treatment products. In various embodiments, a tissue treatment product comprises a collection of elongated elements, each elongated element comprising a tissue matrix that has been at least partially decellularized, and wherein each elongated element has a flexible three-dimensional structure comprising a length dimension, a width dimension, and a height dimension, and wherein one dimension is substantially larger than the other two dimensions (e.g., at least about 2, 3, 4, 5, 10, 20, 50, or 100 times larger, or any value in between). In some embodiments, the tissue treatment products can be used as implants that will conform to the anatomical shape of an implant site while resisting migration away from the site of implantation and/or avoiding significant hardening or raising/swelling of the implant (e.g., due to inflammation and/or the formation of granulation or scar tissue around the implant), as compared to an implanted tissue treatment product that does not comprise elongated or high aspect ratio elements. For example, a hardened and/or raised subcutaneous implant may be cosmetically undesirable or may result in complications that necessitate implant removal.

Various human or other animal tissues and various methods can be used to prepare tissue treatment products. For example, the compositions can be prepared by selecting a human or porcine tissue; decellularizing the tissue to produce a collagen-containing tissue matrix; and applying mechanical forces (e.g., rolling, freezing, and/or cutting acellular tissue) to produce an elongated tissue matrix. For example, one or more sheets of acellular tissue matrix can be rolled into a cylindrical structure of desired length and diameter, frozen, and then optionally sliced, (e.g., on a deli slicer) to produce tissue treatment products whose elements have a high aspect ratio structure. Elongated elements or high aspect ratio elements can comprise a structure having a length dimension, a width dimension, and a height dimension, and wherein one dimension is substantially larger than the other two dimensions (e.g., at least about 2, 3, 4, 5, 10, 20, 50, or 100 times larger, or any value in between).

The compositions produced in this manner can be used, in certain embodiments, to regenerate, repair, heal, augment, reinforce, and/or treat tissues that have been damaged or lost due to various diseases and/or structural damage (e.g., from trauma, surgery, atrophy, and/or long-term wear and degeneration). In some embodiments, the elongated tissue matrices can be folded, compressed, or otherwise molded to fill a desired anatomical shape at a site of implantation. In some embodiments, the elongated elements are capable of being included within a syringe or similar device for injection into an implant. In certain embodiments, the ability of elongated tissue matrices to fill an anatomical space allows for the more preservation of a more natural look or feel after implantation. Furthermore, in various embodiments, the elongated elements of these tissue treatment products resist migration away from the implant site, while also allowing for continued fluid passage and preventing fluid buildup at the implant site. Further, in some embodiments the elongated elements avoid significant hardening or raising/swelling of the implant (e.g., due to inflammation and/or the formation of granulation or scar tissue around the implant), as compared to an implanted tissue treatment product that does not comprise elongated or high aspect ratio elements.

The compositions of the present disclosure can also be used, in certain embodiments, for cosmetic purposes to repair or alter the appearance or feel of a native tissue. In some embodiments, elongated tissue treatment products can be folded, compressed, or otherwise molded to fill a space between separated tissues, regardless of the shape of the space, in various embodiments, the compositions will not migrate away from the site of implantation while also allowing for continued fluid passage and preventing fluid buildup at the implant site.

The materials and methods provided herein can be used to make a biocompatible implant. As used herein, a "biocompatible" composition is one that has the ability to support the migration and proliferation of native cells from surrounding tissue into an implanted tissue treatment product. Biocompatible compositions support native cellular activity necessary for tissue regeneration, repair, healing, or treatment and do not elicit a substantial immune response that prevents such cellular activity. As used herein, a "substantial immune response" is one that prevents partial or complete tissue regeneration, repair, healing, or treatment.

As used herein, the terms "native cells" and "native tissue" mean the cells or tissue present in the recipient organ or tissue prior to implantation of a tissue treatment product, or the cells or tissue produced by the host animal after implantation.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described here will be understood to include the endpoints and all values between the endpoints.

Tissue Treatment Compositions

In certain embodiments, a tissue treatment product is provided. As used herein, a "tissue treatment product" comprises human or animal tissue that has been at least partially decellularized. Tissue treatment products can contain tissue that is acellular, partially decellularized, and/or decellularized tissue that has been repopulated with exogenous cells, so long as the tissue retains at least some of the extracellular matrix scaffold found in native tissue prior to decellula zing.

In some embodiments, the tissue treatment products are processed such that they can conform to the shape of an anatomical implant site. It may be beneficial to conform the shape of the tissue matrices to the desired shape of the anatomical site in a way that is not easily done with a sheet of acellular tissue. Various processes are known to alter the three-dimensional shape of a sheet of acellular tissue, but some of these can also alter the tissue matrix in undesirable ways. For example, chemical cross-linking can be used to alter the three-dimensional structure an acellular tissue matrix, but excessive cross-linking can also alter the biological properties of the tissue, and chemical cross-linking agents may be harmful to patients when implanted in a patient. Accordingly, alternative methods for controlling the shape of tissue treatment products, while preventing migration of the products away from an implant site, would be beneficial and are disclosed herein.

In certain embodiments, a tissue treatment product comprises a collection of elongated elements or subunits (hereafter referred to as an "elongated tissue treatment product"). In some embodiments, each elongated element comprises a tissue matrix that has been at least partially decellularized, and each elongated element has a flexible three-dimensional structure comprising a length dimension, a width dimension, and a height dimension, and wherein one dimension (i.e., the "long axis") is substantially larger than the other two dimensions. The term "substantially" in this context means having a dimension that is at least 10% longer than either of the two remaining dimensions. In some embodiments, the elongated element is at least about 10%, 15%, 20%, 25%, 30%, 35%, 40%, 45%, 50%, 55%, 60%, 65%, 70%, 75%, 100%, 150%, 200%, 250%, 300%, 350%, 400%, 450%, 500%, 750%, 1000%, 2000% or 5000% (or any percentage in between) longer in one dimension. The elongated element can be regular (e.g., an ellipsoid, cylinder, rectangular cuboid, etc.) or irregular (i.e., lacking in uniform structure but generally having one elongated axis). In certain embodiments, the elongated element is in the form of a cylinder prepared from one or more (e.g., 1, 2, 3, 4, 5, 10, 20, or more) rolled pieces or sheets of acellular tissue. The cylinder of rolled acellular tissue can be held in place through natural adhesion, or by freezing, freeze-drying, desiccating, or by any other method of fixing the acellular tissue that is known in the art (e.g., through mild to moderate chemical cross-linking).

In certain embodiments, the elongated elements of a tissue treatment product are further processed to produce elements having a high aspect ratio. As used herein, a "high aspect ratio" element is an element having a three dimensional structure (i.e., a length, a width, and a height), one dimension (i.e., the "long axis") that is substantially larger than the other two dimensions, and two remaining dimensions that are substantially smaller than the long axis and are generally measured in the micrometer to the millimeter range (e.g., two dimensions of less than 50 mm, 40 mm, 30 mm, 20 mm, 15 mm, 10 mm, 5 mm, 4 mm, 3 mm, 2 mm, 1.5 mm, 1 mm, 900 μm, 800 μm, 700 μm, 600 μm, 500 μm, 400 μm, 300 μm, 200 μm, or 100 μm, or any value in between). The term "substantially" in this context means having a long axis that is at least 10% longer than either of the two remaining dimensions. In some embodiments, the high aspect ratio tissue treatment product is at least 50%, 55%, 60%, 65%, 70%, 75%. 100%, 150%, 200%, 250%, 300%, 350%, 400%, 450%, 500%, 750%, 1000%, 2000% or 5000% (or any percentage in between) longer in one dimension.

For example, high aspect ratio elements can be prepared by slicing elongated elements parallel to the long axis or across the face of the two shorter dimensions in order to form thin elements having a long axis and a high aspect ratio (e.g., thin fibers, threads, noodles, or other thin strands) of desired dimensions. See FIG. 1. As used herein, "thin" means having two shorter dimensions that are measured in the micrometer to the millimeter scale (e.g., two dimensions of less than 50 mm, 40 mm, 30 mm, 20 mm, 15 mm, 10 mm, 5 mm, 4 mm, 3 mm, 2 mm, 1.5 mm, 1 mm, 900 μm, 800 μm, 700 μm, 600 μm, 500 μm, 400 μm, 300 μm, 200 μm, or 100 μm, or any value in between). A high aspect ratio element prepared by slicing an elongated element can have a long axis equivalent in length to the long axis or equal in length to the circumference of an elongated element prior to processing, or the high aspect ratio elements product can be further processed (e.g., by manual cutting) to yield a long axis that is shorter than the full length of the long axis or the circumference of the original elongated element.

In certain embodiments, the high aspect ratio elements can be organized to form a mesh, weave, or other tertiary structure. For example, high aspect ratio strands can be twined to form a larger mesh of acellular tissue. As used herein, a "mesh" is any composition comprising woven or interconnected strands of biological fibers. One of skill in the art will recognize that the tightness of the weave or mesh will vary depending on the desired physical properties of the tertiary structure (e.g., mechanical strength, porosity, flexibility, etc.). In other embodiments, the high aspect ratio strands of a tissue treatment product are kept in a loose concentration (i.e., without an organized tertiary structure) for ease of separation and/or surgical delivery into an implant site.

Tissue treatment products can comprise elements having an acellular tissue matrix and/or elements having an intact or partially decellularized tissue matrix. In one embodiment, the tissue treatment product comprises elements having an acellular dermal tissue matrix. In certain embodiments, the tissue from which the acellular or partially decellularized tissue matrix is derived is selected from one or more of fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, skin, dermal, subdermal tissue, heart tissue, lung tissue, liver tissue, and intestinal tissue.

In various embodiments, a tissue treatment product comprises elongated elements having a flexible three-dimensional shape that can conform to the anatomic structure of an implant site. For example, tissue treatment products can be useful to support breast implants, e.g., for use in breast augmentation and/or reconstruction. For example, a tissue treatment product having elongated or high aspect ratio elements can be placed around a breast implant and used to fill the space between the implant and surrounding native tissue, thereby providing a smoother contour and/or more natural look and feel for the implant. The elongated or high aspect ratio elements within a tissue treatment product can either naturally resist migration from their position surrounding an implant, or they can be attached (e.g., with sutures) to surrounding fascia, muscle, or other native tissue, thereby helping to secure an implant in a proper position, to reduce or prevent scar formation, or to otherwise alter the aesthetic appearance of an implant.

Tissue treatment products can be selected to provide a variety of different biological and mechanical properties. For example, a tissue treatment product can be selected in order to provide a scaffold in which native cells from tissue surrounding an implanted tissue treatment product can migrate and proliferate, thereby enhancing the speed or overall level of repair, regeneration, healing, or treatment of native tissue. For example, an acellular tissue matrix, when implanted on or into fascia, may be selected to allow for regeneration of the fascia without excessive inflammation, fibrosis or scar tissue formation (e.g., by selecting a fully decellularized tissue product). In some embodiments, the loose, porous structure of an elongated or high aspect ratio acellular tissue treatment product avoids the obstruction and subsequent build up of fluid within the implant site, while also providing a scaffold for native cells, tissue, and vasculature to migrate and proliferate. In some embodiments, the elongated or high aspect ratio acellular tissue treatment products resist migration away from the implant site.

In certain embodiments, the elongated or high aspect ratio tissue treatment products of the present disclosure can be molded to adapt to any desired three-dimensional structure (e.g., to fill the anatomical structure of an implant site) without requiring undesirable chemical alterations in the tissue matrix. In various embodiments, the elongated or high aspect ratio elements within a tissue treatment product are capable of substantial stretching, torsion, or compression. In some embodiments, the elongated or high aspect ratio elements within a tissue treatment product are capable of rapidly returning to their original dimensions after the release of a compression, tension, or torsion force. In some embodiments, the elongated or high aspect ratio tissue treatment products can be molded into and maintain a three-dimensional structure without excessive crosslinking. Although cross-linking may assist in maintaining a desired three-dimensional shape, excessive crosslinking can alter the biological properties of tissue treatment products. In some embodiments, elongated or high aspect ratio elements are joined to form desired three dimensional structures (e.g., spheres, columns, or other shapes intended to match anatomical implant sites) using natural adhesion, or by freezing, freeze-drying, desiccating, or by any other method of fixing the three dimensional shape of acellular tissue that is known in the art (e.g., through mild to moderate chemical cross-linking)

Tissue crosslinking can be measured by an increase in the denaturation temperature of a tissue matrix, as measured with differential scanning calorimetry. Accordingly, in some embodiments, tissue treatment products of the present disclosure include an acellular or partially decellularized tissue matrix that has a denaturation temperature, as measured by differential scanning calorimetry, that is within 5° C. (i.e., within 5° C., 4° C., 3° C., 2° C., or 1° C., or any temperature in between) of the denaturation temperature of the tissue from which the matrix is produced.

The extracellular matrix within the elements of a tissue treatment product may consist of collagen, elastin, and/or other fibers, as well as proteoglycans, polysaccharides and/or growth factors. In some embodiments, the acellular tissue matrix may retain some or all of the extracellular matrix components that are found naturally in a tissue prior to decellularization, or various undesirable components may be removed by chemical, enzymatic or genetic means. In general, the acellular matrix provides a structural network on which native tissue and vasculature can migrate, grow, and proliferate. The exact structural components of the extracellular matrix will depend on the tissue selected and the processes used to prepare the acellular tissue.

A tissue treatment product can be derived from any tissue that is suitable for decellularization and subsequent implantation. Exemplary tissues include, but are not limited to, bone, skin, dermis, intestine, urinary bladder, tendon, ligament, muscle, fascia, neurologic tissue, vessel, liver, heart, lung, kidney, cartilage, and/or any other suitable tissue. In certain embodiments, the tissue treatment product can include a mammalian soft tissue. For example, in certain embodiments, the tissue treatment product can include partially or completely decellularized mammalian dermis. In other embodiments, the tissue treatment product can comprise partially or completely decellularized small intestine submucosa. In certain embodiments, the decellularized tissue can come from human or non-human sources. Exemplary, suitable non-human tissue sources include, but are not limited to, pigs, sheep, goats, rabbits, monkeys, and/or other non-human mammals.

In certain embodiments, tissue treatment products can be formed from ALLODERM® or STRATTICE™, which are human and porcine acellular dermal matrices respectively (Lifecell Corp., Branchburg, N.J.). Alternatively, any other suitable acellular tissue matrices can be used. For example, a number of biological scaffold materials are described by Badylak et al., and the methods of the present disclosure can be used to produce a stable three-dimensional acellular tissue matrix using any of those materials, or any other similar materials. Badylak et al., "Extracellular Matrix as a Biological Scaffold Material: Structure and Function," *Acta Biomaterialia* (2008), doi:10.1016/j.actbio.2008.09.013, hereby incorporated by reference in its entirety.

In certain embodiments, a tissue treatment product lacks certain undesirable antigens. For example, certain animal tissues contain alpha-galactose (α-gal) epitopes that are known to elicit reactions in humans. Therefore, acellular tissue treatment products derived from various animal tissues can be produced or processed to lack certain antigens, such as α-gal. In some embodiments, tissue treatment products lack substantially all α-gal moieties. Elimination of the α-gal epitopes from a tissue treatment product may diminish the immune response against the composition. U. Galili et al., *J. Biol. Chem.* 263: 17755 (1988). Since non-primate mammals (e.g., pigs) produce α-gal epitopes, xenotransplantation of acellular tissue matrix material from these mammals into primates may result in rejection because of primate anti-Gal binding to the α-gal epitopes on the acellular tissue matrix. The binding results in the destruction of the acellular tissue by complement fixation and by antibody-dependent cell cytotoxicity. U. Galili et al., *Immunology Today* 14: 480 (1993); M. Sandrin et al., *Proc. Natl. Acad. Sci, USA* 90: 11391 (1993); H. Good et al., *Transplant. Proc.* 24: 559 (1992); B. H. Collins et al., *J. Immunol.* 154: 5500 (1995).

As described in detail below, in various embodiments, tissue treatment products can be processed to remove antigens such as α-gal, e.g., by chemical or enzymatic treatment. Alternatively, tissue treatment products can be produced from animals that have been genetically modified to lack these epitopes.

In various embodiments, tissue treatment products have reduced bioburden (i.e., a reduced number of microorganisms growing on the compositions). In some embodiments, tissue treatment products lack substantially all bioburden (i.e., the tissue treatment products are aseptic or sterile). As used herein, "lacking substantially all bioburden" means tissue treatment products in which the concentration of growing microorganisms is less than 1%, 0.1%, 0.01%, 0.001%, or 0.0001% (or any percentage in between) of that growing on untreated tissue treatment products.

In certain embodiments, tissue treatment products are completely or substantially free of all cells normally present in the tissue from which the tissue treatment product is derived. As used herein, "substantially free of all cells" means that the tissue treatment product contains less than 20%, 10%, 5%, 1%, 0.1%, 0.01%, 0.001%, or 0.0001% (or any percentage in between) of the cells that normally grow within the acellular matrix of the tissue prior to decellularization.

In some embodiments, tissue treatment products can include partially decellularized tissue matrices and/or decellularized tissue matrices that have been repopulated with viable cells. Various cell types can be used for repopulation, including stem cells such as embryonic stem cells, adult stem cells (e.g. mesenchymal stem cells), and/or neuronal cells. Any other viable cells that are histocompatible with the patient in which they are being implanted can also be used. In some embodiments, the histocompatible cells are mammalian cells. Such cells can promote native tissue migration, proliferation, and/or vascularization. In various embodiments, the viable cells are applied to the acellular tissue matrix before or after implantation of a tissue treatment product.

In certain embodiments, the tissue treatment products comprises one or more additional agents. In some embodiments, the additional agent can comprise an anti-inflammatory agent, an analgesic, or any other desired therapeutic or beneficial agent. In certain embodiments, the additional agent can comprise, e.g., at least one added growth or signaling factor (e.g., a cell growth factor, an angiogenic factor, a differentiation factor, a cytokine, a hormone, and/or a chemokine). These additional agents can promote native tissue migration, proliferation, and/or vascularization. In some embodiments, the growth or signaling factor is encoded by a nucleic acid sequence contained within an expression vector. Preferably, the expression vector is in one or more of the viable cells that can be added, optionally, to a tissue treatment product. As used herein, the term "expression vector" refers to any nucleic acid construct that is capable of being taken up by a cell, contains a nucleic acid sequence encoding a desired protein, and contains the other necessary nucleic acid sequences (e.g. promoters, enhancers, initiation and termination codons, etc.) to ensure at least minimal expression of the desired protein by the cell.

Tissue treatment products, as described above, can be provided in some embodiments in packaged, hydrated, frozen, freeze-dried, and/or dehydrated form. In certain embodiments, the packaged tissue treatment products are sterile. In certain embodiments, the tissue treatment products are provided in a kit, comprising a packaged tissue treatment product and instructions for preparing and/or using the tissue treatment products.

Methods of Production

Disclosed herein are methods of making tissue treatment products comprising elongated and/or high aspect ratio elements. In some embodiments, the method comprises selecting a tissue containing an extracellular collagen matrix; partially or completely decellularizing the tissue; and applying mechanical forces to the tissue matrix to produce the elongated or high aspect ratio elements of the tissue treatment product.

A tissue treatment product can be prepared from any tissue that is suitable for decellularization and subsequent implantation. Exemplary tissues include, but are not limited to, at least one of bone, skin, adipose, dermis, subdermal tissue, intestine, urinary bladder, tendon, ligament, muscle, fascia, neurologic tissue, vessel, liver, heart, lung, kidney, cartilage, and/or any other suitable tissue. In certain embodiments, the tissues can include a mammalian soft tissue. For example, in certain embodiments, the tissue can comprise mammalian dermis. In certain embodiments, the dermis can be separated from surrounding epidermis and/or other tissues, such as subcutaneous fat. In certain embodiments, the tissue can comprise small intestine submucosa. In certain embodiments, the tissue can include human and/or non-human sources. Exemplary, suitable non-human tissue sources include, but are not limited to, pigs, sheep, goats, cow, rabbits, monkeys, and/or other non-human mammals, In some embodiments, a tissue treatment product is prepared by harvesting and partially or completely decellularizing a donor tissue. Exemplary methods for decellularizing tissue are disclosed in U.S. Pat. No. 6,933,326 and U.S. Patent Application 2010/0272782, which are hereby incorporated by reference in their entirety. In some embodiments, the decellularized tissue provides a porous extracellular scaffold structure into which cells from surrounding native tissue can migrate and proliferate after implantation of a tissue treatment product into a host site. In certain exemplary embodiments, the acellular tissue comprises ALLODERM® or STRATTICE™, which are acellular human dermal products and porcine dermal products, respectively, and are available from LifeCell Corporation (Branchburg, N.J.).

In various embodiments, the general steps involved in the production of an acellular tissue matrix include harvesting tissue from a donor (e.g., a human cadaver or animal source) and removing cells under conditions that preserve biological and structural function. In certain embodiments, the harvested tissue can be washed to remove any residual cryoprotectants and/or other contaminants. Solutions used for washing can be any physiologically-compatible solution. Examples of suitable wash solutions include distilled water, phosphate buffered saline (PBS), or any other biocompatible saline solution.

In certain embodiments, the decellularization process includes chemical treatment to stabilize the harvested tissue so as to avoid biochemical and structural degradation before, during, or after cell removal. In various embodiments, the stabilizing solution arrests and prevents osmotic, hypoxic, autolytic, and/or proteolytic degradation; protects against microbial contamination; and/or reduces mechanical damage that can occur during decellularization of tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

In various embodiments, the tissue is then placed in a decellularization solution to remove viable cells (e.g., epithelial cells, endothelial cells, smooth muscle cells, and fibroblasts, etc.) from the extracellular matrix without damaging the biological and/or structural integrity of the extracellular matrix. The decellularization solution may contain an appropriate buffer, salt, an antibiotic, one or more detergents (e.g., TRITON X-100™, sodium dodecyl sulfate, sodium deoxycholate, polyoxyethylene (20) sorbitan mono-oleate, etc.), one or more agents to prevent cross-linking, one or more protease inhibitors, and/or one or more enzymes. In some embodiments, the decellularization solution comprises 0.1%, 0.2%, 0.3%, 0.4%, 0.5%, 1.0%, 1.5%, 2.0%, 2.5%, 3.0%, 3.5%, 4.0%, 4.5%, or 5.0% (or any percentage in between) of TRITON X-100™ and, optionally, 10 mM, 15 mM, 20 mM, 25 mM, 30 mM, 35 mM, 40 mM, 45 mM, or 50 mM EDTA (ethylenediaminetetraacetic acid) (or any concentration in between). In some embodiments, the tissue is incubated in the decellularization solution at 25, 30, 31, 32, 33, 34, 35, 36, 37, 38, 39, 40, 41, or 42° C. (or any temperature in between), and optionally with gentle shaking at 10, 20, 30, 40, 50, 60, 70, 80, 90, 100, 110, 120, 130, 140, or 150 rpm (or any rpm in between). The incubation can be for 1, 2, 3, 4, 5, 6, 7, 8, 9, 10, 11, 12, 15, 20, 24, 36, or 48 hours (or any time in between). The length of time or concentration of detergent can be adjusted in order to partially or more fully decellularize the tissue. In certain embodiments, additional detergents may be used to remove fat from the tissue sample. For example, in some embodiments, 1, 2, 3, 4, or 5% sodium deoxycholate (or any percentage in between) is added to the decellularization solution in order to remove fat from the tissue.

In some embodiments, after decellularization, the tissue sample is washed thoroughly. Any physiologically-compatible solutions can be used for washing. Examples of suitable wash solutions include distilled water, phosphate buffered saline (PBS), or any other biocompatible saline solution. In certain embodiments, e.g., when xenogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable DNase buffer can be used, as long as the buffer provides for suitable DNase activity.

While an acellular tissue matrix may be derived from tissue from one or more donor animals of the same species as the intended recipient animal, this is not necessarily the case.

Thus, for example, an acellular tissue matrix may be derived from porcine tissue and implanted in a human patient. Species that can serve as donors and/or recipients of acellular tissue matrices include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

In certain embodiments, decellularized tissue can be treated with one or more enzymes to remove undesirable antigens, e.g., an antigen not normally expressed by the recipient animal and thus likely to lead to an immune response and/or rejection of the implanted tissue treatment product. For example, in certain embodiments, decellularized tissue can be treated with alpha-galactosidase to remove alpha-galactose ($\alpha$-gal) moieties. In some embodiments, to enzymatically remove $\alpha$-gal epitopes, after washing tissue thoroughly with saline, the tissue may be subjected to one or more enzymatic treatments to remove $\alpha$-gal antigens, if present in the sample. In certain embodiments, the tissue may be treated with an $\alpha$-galactosidase enzyme to eliminate $\alpha$-gal epitopes. In one embodiment, the tissue is treated with $\alpha$-galactosidase at a concentration of 0.2 U/ml prepared in 100 mM phosphate buffered saline at pH 6.0. In other embodiments, the concentration of $\alpha$-galactosidase is reduced to 0.1 U/ml or increased to 0.3, 0.4, or 0.5 U/ml (or any value in between). In other embodiments, any suitable enzyme concentration and buffer can be used, as long as sufficient antigen removal is achieved. In addition, certain exemplary methods of processing tissues to reduce or remove alpha-1,3-galactose moieties are described in Xu et al., *Tissue Engineering*, Vol. 15, 1-13 (2009), which is hereby incorporated by reference in its entirety.

In certain embodiments, animals that have been genetically modified to lack one or more antigenic epitopes may be selected as the tissue source for a tissue treatment product. For example, animals (e.g., pigs) that have been genetically engineered to lack the terminal $\alpha$-galactose moiety can be selected as the tissue source. For descriptions of appropriate animals and methods of producing transgenic animals for xenotransplantation, see U.S. patent application Ser. No. 10/896,594 and U.S. Pat. No. 6,166,288, which are hereby incorporated by reference in their entirety.

In some embodiments, the decellularized tissue can be treated to reduce bioburden (i.e., to reduce the number of microorganisms growing on the tissue). In some embodiments, the tissue is treated such that it lacks substantially all bioburden (i.e., the tissue is aseptic or sterile), As used herein, "substantially all bioburden" means that the concentration of microorganisms growing on the tissue is less than 1%, 0.1%, 0.01%, 0.001%, or 0.0001% of that growing on untreated tissue, or any percentage in between. Suitable bioburden reduction methods are known to one of skill in the art, and may include exposing the tissue treatment product to radiation. Irradiation may reduce or substantially eliminate bioburden. In some embodiments, an absorbed dose of 15-17 kGy of E-beam radiation is delivered in order to reduce or substantially eliminate bioburden. In various embodiments, the amount of radiation to which the tissue treatment product is exposed can be between 5 Gy and 50 kGy. Suitable forms of radiation can include gamma radiation, e-beam radiation, and X-ray radiation. Other irradiation methods are described in U.S. Application 2010/0272782, the disclosure of which is hereby incorporated by reference in its entirety.

In certain embodiments, after the acellular tissue matrix is formed, histocompatible, viable cells may optionally be seeded in the acellular tissue matrix. In some embodiments, histocompatible viable cells may be added to the matrices by standard in vitro cell co-culturing techniques prior to transplantation, or by in vivo repopulation following transplantation. In vivo repopulation can be by the migration of native cells from surrounding tissue into the acellular tissue matrix or by infusing or injecting histocompatible cells obtained from the recipient or from another donor into the acellular tissue matrix in situ. Various cell types can be used, including stem cells such as embryonic stem cells and/or adult stem cells (e.g. mesenchymal stem cells). Any other viable cells that are histocompatible with the patient in which they are being implanted can also be used. In some embodiments, the histocompatible cells are mammalian cells. Such cells can promote native tissue migration, proliferation, and/or vascularization. In various embodiments, the cells can be directly applied to the acellular tissue matrix just before or after implantation.

In certain embodiments, one or more additional agents can be added to the acellular tissue matrix. In some embodiments, the additional agent can comprise an anti-inflammatory agent, an analgesic, or any other desired therapeutic or beneficial agent. In certain embodiments, the additional agent can comprise at least one added growth or signaling factor (e.g., a cell growth factor, an angiogenic factor, a differentiation factor, a cytokine, a hormone, and/or a chemokine). These additional agents can promote native tissue migration, proliferation, and/or vascularization. In some embodiments, the growth or signaling factor is encoded by a nucleic acid sequence contained within an expression vector. Preferably, the expression vector in one or more of the viable cells that can be included, optionally, along with the acellular tissue matrix. As used herein, the term "expression vector" refers to any nucleic acid construct that is capable of being taken up by a cell, contains a nucleic acid sequence encoding a desired protein, and contains the other necessary nucleic acid sequences (e.g. promoters, enhancers, termination codon, etc.) to ensure at least minimal expression of the desired protein by the cell.

In various embodiments, either before or after decellulanzation, the acellular tissue matrix can be shaped and/or processed into a desired form, such as an elongated structure. Accordingly, a method is provided for shaping an acellular tissue matrix. In some embodiments, acellular tissue can be rolled, packed, folded, compressed or otherwise molded into a desired shape, such as a ball, cube, cylinder, ellipsoid, rectangular cuboid, or any other regular or irregular shape. One or more separate pieces of acellular tissue (e.g., 1, 2, 3, 4, 5, 10, or more pieces) can be incorporated into the desired shape. For example, one or more pieces of acellular tissue (e.g., 1, 2, 3, 4, 5, 10, or more pieces) can be rolled into a cylinder or into a similar elongated shape in order to form an elongated element of a tissue treatment product. The rolled tissue can retain its shape by natural adhesion, or by freezing, freeze-drying, desiccating, or by any other method of fixing the acellular tissue that is known in the art (e.g., through mild to moderate chemical cross-linking)

In certain embodiments, the elongated elements of a tissue treatment product can be further processed to produce elements having a high aspect ratio. For example, the elongated elements can be sliced (e.g., using a knife, deli slicer, grater, etc.) parallel to their long axis or across the face of their two smaller dimensions in order to form thin elements having a long axis and a high aspect ratio (e.g., a "noodle" structure). As used herein, a high aspect ratio means having two dimensions that are measured in the micrometer to the millimeter scale (e.g., two dimensions of less than 50 mm, 40 mm, 30 mm, 20 mm, 15 mm, 10 mm, 5 mm, 4 mm, 3 mm, 2 mm, 1 mm, 900 µm, 800 µm, 700 µm, 600 µm, 500 µm, 400 µm, 300

μm, 200 μm, or 100 μm, or any value in between). The high aspect ratio elements of a tissue treatment product produced in this way can have a long axis equivalent to the length of the circumference or long axis of an elongated element product prior to slicing, or the high aspect ratio elements can be further processed (e.g., by manual cutting) to yield a long axis that is shorter than the full length of the long axis or circumference of the original elongated elements. In some embodiments, the long axis of the high aspect ratio element has a dimension that is at least 50% longer than either of the two remaining dimensions. In some embodiments, the high aspect ratio element is at least about 50%, 55%, 60%, 65%, 70%, 75%, 100%, 150%, 200%, 250%, 300%, 350%, 400%, 450%, 500%, 750%, 1000%, 2000% or 5000% (or any percentage in between) longer in one dimension.

In some embodiments, elongated cylindrical elements containing one or more pieces or sheets of rolled and frozen acellular tissue are sliced (e.g. using a knife, deli slicer, grater, etc.) to form the high aspect ratio elements of a tissue treatment product. The slicing can be done at a desired thickness to produce high aspect ratio elements of desired dimensions. In some embodiments, the high aspect ratio elements can have a long axis equivalent to the length of the circumference of the frozen cylindrical elements. In other embodiments, the high aspect ratio elements can be cut (e.g., using a knife, scalpel, or other blade) such that their long-axis length is shortened.

In certain embodiments, a device for slicing, such as a deli slicer, is used to slice across the circular face of a cylinder of rolled acellular tissue, thereby producing high aspect ratio elements (e.g., "noodles") of predetermined thickness, where the thickness depends on the thickness setting of the device used to slice the cylinder. In some embodiments, the cylinder of rolled acellular tissue is frozen to allow for easier slicing (e.g., to allow for more consistent slicing).

In certain embodiments, the high aspect ratio elements of a tissue treatment product can be further processed to form a mesh, weave, or other tertiary structure. For example, high aspect ratio strands can be twined to form a larger mesh of acellular tissue. As used herein, a "mesh" is any composition comprising woven or interconnected strands of biological fibers. One of skill in the art will recognize that the tightness of the weave or mesh can vary depending on the desired physical properties of the tertiary structure (e.g., mechanical strength, porosity, flexibility, etc.). In some embodiments, the tertiary structure is held together by natural adhesion, or by freezing, freeze-drying, desiccating, or by any other method of fixing the acellular tissue that is known in the art (e.g., through mild to moderate chemical cross-linking). In other embodiments, the high aspect ratio elements of a tissue treatment product are kept in a loose concentration (i.e., without an organized tertiary structure) for ease of separation and/or surgical delivery into an implant site.

Methods of Use

An objective when using tissue-derived products to regenerate, repair, heal, or otherwise treat diseased or damaged tissues and organs is to provide an implant capable of maintaining shapes or configurations that more closely conform to the anatomic structures that are being treated, while also reducing or avoiding implant migration away from the implant site. Accordingly, disclosed in certain embodiments are methods of using tissue treatment products comprising collections of elongated or high aspect ratio elements as fillers to pack a void space, wound, or other tissue in need of treatment, repair, healing, or regeneration. As used herein, a "collection" means at least 2 pieces or elements (e.g., at least 2, 3, 4, 5, 6, 7, 8, 9, 10, 15, 20, 25, 30, 35, 40, 45, 50, 75, or 100 pieces, or any number in between). The individual pieces of tissue within the collection can have the same or different structures. The tissue treatment product comprising a collection of elongated or high aspect ratio tissuenatrices can be molded to fill a desired shape while reducing the risk that the implant will migrate away from the implant site. In some embodiments, the tissue treatment product can also be used for cosmetic or enhancement purposes (e.g., as a cosmetic implant or as an adjunct to a traditional cosmetic implant).

In certain embodiments, following the creation of space between tissue planes as a result of disease, trauma, or surgical intervention, a tissue treatment product comprising one or a collection of elongated or high aspect ratio elements is placed between the separated tissue planes. In certain embodiments, the implanted tissue treatment product can be used to completely fill and conform to the shape of a space in a host tissue. In some embodiments, the product can be folded, compressed, or otherwise molded to fill the anatomical space of an implant site.

In certain embodiments, the elements of an implanted tissue treatment product can have an organized tertiary structure, such as a mesh, weave or other organized structure, or the elements can be present in a loose form lacking an organized tertiary structure. In some embodiments, the tissue treatment products can be folded, compressed, packed, or otherwise molded to fill the space between separated tissue planes, regardless of the shape of the space (e.g., an irregularly shaped wound can be filled with a tissue treatment product until all space within the wound is filled with tissue treatment product). In one example, the implanted tissue treatment product comprises elements having a high aspect ratio. In certain embodiments, the high aspect ratio elements can be folded, compressed, or otherwise molded within an implant site until all void space in the implant site is filled. In some embodiments, the high aspect ratio elements can also be organized in a mesh, weave or other organized tertiary structure.

In some embodiments, a tissue treatment product can be used for tissue bulking (e.g., to fill space surrounding a breast implant or as supporting material between bone and cartilage or in the submucosal layer of the nasal passage following otolaryngology surgery). In other embodiments, tissue treatment products are used to completely fill void space (e.g., after tumor removal), to bulk native tissue (e.g., for nasal reconstruction), or for aesthetic tissue enhancement purposes (e.g., as a complement to breast implants that is used to smooth contours and fill space surrounding the implant).

In certain embodiments, a tissue treatment product is implanted in a host tissue and remains in place through the natural tendency of the elongated or high aspect ratio elements to resist migration away from the implant site. In other embodiments, tissue treatment products are secured to the native tissue planes that surround an implant site using any known method that results in the temporary or permanent physical association of the tissue treatment products with the proximate tissue. For example, biodegradable sutures can be used to physically secure the tissue treatment product to the surrounding native tissue. Alternatively, external positive pressure (e.g., a dressing or binding around the implant site) can be applied to compress the surrounding native tissue and maintain the native tissue in contact with the implanted tissue treatment products, thereby preventing migration of the tissue treatment products away from the implant site.

One benefit of implanting a tissue treatment product comprising a collection of elongated or high aspect ratio elements is that the elongated or high aspect ratio structure of these elements can prevent or reduce the tendency of an implant to migrate away from the implant site. Thus, in some embodiments, tissue treatment products can be used without requiring undesirable chemical modification or physical attachment to native tissue that is otherwise necessary in order to prevent migration away from an implant site. In various embodiments, the ability to retain a tissue treatment product at an implant site without requiring chemical or physical intervention (e.g., cross-linking or suturing) can be important when using a tissue treatment product to fill void space (e.g., after tumor removal), to bulk native tissue (e.g., for nasal reconstruction), or for aesthetic tissue enhancement purposes (e.g., as a complement to breast implants that is used to smooth contours and fill space surrounding the implant). In these contexts, tissue treatment products can be implanted and will not migrate from the implant site, while still avoiding the irritation or loss of biocompatibility associated with chemical or physical processing to secure an implant to surrounding tissue.

In certain embodiments, a tissue treatment product comprising a collection of high aspect ratio elements (e.g., "noodles") is used. The flexible strands of the high aspect ratio tissue treatment products can be folded, compacted, and/or molded to fill an implant site. The high aspect ratio elements allow for continued fluid mobility within the implant site, thereby preventing undesirable fluid accumulation. At the same time, the high aspect ratio elements provide an acellular scaffold in which native cells and vasculature can migrate and proliferate, thereby promoting or enhancing tissue repair, regeneration, and/or healing. Also, the high aspect ratio structure of the elements can prevent the tissue treatment product from migrating away from the implant site, without requiring the use of chemical cross-linking agents or other interventions designed to immobilize the tissue treatment product. For example, tissue treatment products comprising a collection of high aspect ratio elements can be used to fill the space surrounding a breast implant. The high aspect ratio tissue treatment products can be used in this context to support the breast implant and keep the implant from shifting from the appropriate location, while also providing a more natural look and feel to the implant by filling the space between the breast implant and surrounding tissue, for example by avoiding and/or reducing inflammation, or the formation of granulation or scar tissue surrounding the implant that could result in an undesirably hardened or raised implant. In another example, the high aspect ratio tissue treatment products can be used to pack a wound or other space between separated tissues resulting from disease, damage, or surgical intervention.

In some embodiments, use of a tissue treatment product comprising a collection of elongated or high aspect ratio elements can result in an implant that has increased persistence in the site of implantation, as compared to implanted sheets of acellular tissue. Persistence refers to the volume of implanted material that remains at a site of implantation over time. Persistence can be measured in various ways that will be familiar to one of skill in the art. For example, persistence of the tissue treatment product at the site of implantation can be measured using ultrasound in order to calculate the volume of tissue treatment product remaining at an implant site over time.

In some embodiments, use of a tissue treatment product comprising a collection of elongated or high aspect ratio elements can result in an implanted tissue treatment product that has improved biomechanical properties, as compared to implanted sheets of acellular tissue. Biomechanical properties can be evaluated in various ways that will be familiar to one of skill in the art. For example, the softness of an implant over time can be evaluated by looking at the tonometry of the implant (i.e., the level of displacement that occurs when the implant is placed under load). For example, indentation tonometry can be used, involving the measurement of the depth of indentation produced by a rod of known weight when placed above the site of implantation. A larger indentation value indicates a softer implant site, while a lower value indicates a harder site. Likewise, in another example the stiffness of the implant over time can be evaluated using the BTC-2000™ (SRLI Technologies, Nashville, Tenn.), which can be used to measure stiffness and other biomechanical properties of skin and underlying soft tissue. In some embodiments, an implanted tissue treatment product comprising a collection of elongated or high aspect ratio elements can result in a firmer implant site, as compared to surrounding tissue.

In certain embodiments, high aspect ratio tissue treatment products that have been organized to form a mesh, weave, or other tertiary structure are implanted in a host tissue. The mesh, weave, or other tertiary structure can be used to fill the site of implantation. For example, a mesh can be used to pack a wound or other space between separated tissues resulting from disease, damage, or surgical intervention. The flexible mesh can be compacted to more tightly fill a space between separated tissues or can be used to provide structural support and reinforcement for a tissue following removal of native tissue from the site of implantation. For example, following tumor removal, a mesh or woven tissue treatment product can be used to fill the space left after surgical intervention and to reinforce the structure of the remaining tissue at the site of implantation. For example, following breast surgery (e.g., lumpectomy), a mesh or woven tissue treatment product can be implanted to preserve the structural appearance and feel of the breast, and to promote native tissue regeneration. In certain embodiments, the mesh, weave, or other tertiary structure allows for continued fluid mobility within the implant site, thereby preventing undesirable fluid accumulation. At the same time, the mesh, weave, or other tertiary structure provides an acellular scaffold in which native cells and vasculature can migrate and proliferate, thereby promoting or enhancing tissue repair, regeneration, and/or healing. Also, in some embodiments, the mesh structure prevents the tissue treatment product from migrating away from the site of implantation; the use of chemical cross-linking agents or other interventions to immobilize the tissue treatment product may not be required in these embodiments.

In various embodiments, a tissue treatment product comprising a collection of elongated or high aspect ratio elements is used after surgical removal of a tumor. In some embodiments, the tumor is a breast tumor. In other embodiments, the tumor is an abdominal or dermal tumor, or any other tumor for which surgical removal is indicated and subsequent replacement with a tissue filler is desirous. In various embodiments, the tissue treatment products are used to fill the space left by surgical removal of a tumor. The tissue treatment products can be used, in some embodiments, to fill the space left by tumor removal while also allowing for continued fluid mobility within the implant site, thereby preventing undesirable fluid accumulation. At the same time, the tissue treatment products provide an acellular scaffold in which native cells and vasculature can migrate and proliferate, thereby promoting or enhancing tissue repair, regeneration, and/or healing. Also, in certain embodiments, the elongated or high aspect ratio structure of the elements within a tissue treatment product can prevent the tissue treatment product from migrating away from the site of implantation; the use of chemical crosslinking agents or other interventions to immobilize the tissue treatment products is not required in these embodiments.

In certain embodiments, a tissue treatment product comprising a collection of elongated or high aspect ratio elements is used to fill a space between separated tissue planes that results from surgical intervention, disease, or trauma. For example, the tissue treatment products can be used to fill a wound or to pack the space between tissue planes that have been separated during surgery. The tissue treatment products provide an acellular scaffold in which native cells and vasculature can migrate and proliferate, thereby promoting or enhancing tissue repair, regeneration, and/or healing. At the same time, the tissue treatment products allow for continued fluid mobility within the implant site, thereby preventing undesirable fluid accumulation. Also, the elongated or high aspect ratio structure of the collection of elements within a tissue treatment product prevents the tissue treatment product from migrating away from the site of implantation; the use of chemical cross-linking agents or other interventions to immobilize the tissue treatment product is not required in these embodiments.

In various embodiments, tissue treatment products comprising a collection of elongated or high aspect ratio elements are used for aesthetic purposes. For example, the tissue treatment products can be used alone or in conjunction with additional implant materials to enhance or alter the shape, texture, softness, elasticity, rigidity, contours, or other properties of tissue in the breast, lips, nose, buttocks, or any other tissue. For example, tissue treatment products can be used to fill the space between a traditional breast implant and surrounding tissue in order to provide a more natural look and feel while preventing fluid accumulation in the empty space around the implant. Likewise, in certain embodiments, tissue treatment products can be used to fill the space between a traditional implant and surrounding tissue in order to support and anchor the traditional implant and prevent it from moving or distorting after implantation. In some embodiments, the tissue treatment products can also promote native tissue repair, regeneration, and/or healing around a traditional implant by providing an acellular scaffold in which native cells and vasculature can migrate and proliferate. In some embodiments, the implanted tissue treatment products do not interfere with clinical mammography.

EXAMPLES

The following examples serve to illustrate, and in no way limit, the present disclosure.

Example 1a

Preparation of Tissue Treatment Products

Approximately 500 g of porcine acellular dermal tissue (PADM) sheets were rinsed and washed and then treated with PRTM Freeze solution at a 5:1 solution to tissue ratio for 6 hours to 36 hours. The acellular porcine dermal tissue sheets were then rolled into a cylinder and placed at −80° C. overnight. A deli slicer was assembled inside a clean room and thoroughly cleaned using Spor-Klenz and 70% IPA.

A sharp and clean deli slicer was used to slice frozen PADM. To keep the deli slicer cold, liquid nitrogen gas was allowed to flow behind the deli slicer's cutting blade. The frozen cylinder of acellular tissue was placed inside a container such as a syringe to help in handling during cutting, and was sliced on the deli slicer to produce tissue treatment products having a high aspect ratio, e.g., a shape similar to a "noodle." The circular face of the rolled cylinder of frozen tissue was kept flat and the cylinder was kept perpendicular to the slicer's cutting blade. The thickness of the high aspect ratio tissue produced in this manner could be varied by altering the deli slicer setting. The deli slicer was set to 1.5 mm diameter depth and rolled cylinders of tissue were sliced individually or bundles of rolled cylinders were sliced together.

After slicing, half the noodles were washed in a preservative solution and the other half in PBS. Noodles were washed twice in each solution for 2 hours. Each wash was in a 5:1 solution to tissue ratio, agitated at 100 rpm. Washed noodles were stored at 4° C.

Hydrated noodles were weighed out and aseptically packed inside a syringe. For bioburden testing, half the contents of the syringe was extruded into a sterile bag, with the remaining half retained in the syringe and saved for sterilization and Implantation. The syringes were placed in foil-to-foil pouches for sterilization and were E-beam irradiated at 15.9-21.5 kGy.

Example 1b

Preparation of Tissue Treatment Products

STRATTICE™ (Lifecell Corp.) was preconditioned by hand cutting into 2 inch by 2 inch samples. Samples were passed through bench top meat grinder with 5/16 inch cutter setting, then passed a second time through the grinder with a 3/16 inch setting. Tissue was sent to Sympak Group (Mundelein, Ill.) for further microcutting using 0.35 and 0.9 mm cut settings. The final cut tissue tended to clump and formed longer "fibers" when rolled together.

Example 2

Yucatan Minipig Mammary Gland Testing

Yucatan minipig mammary glands were used to simulate clinical lumpectomy and to test and compare different implanted tissue treatment products used in vivo to treat lumpectomy defects. Four 20 cc defects per animal were created using electrocautery. Each defect was filled with one of six different tissue treatment products comprising PADM tissue filler materials (noodles in PBS, noodles in a preservative solution, fiber putty in PBS, fiber putty in a preservative solution, consolidated fiber strands (CFS) and acellular sheets of STRATTICE®) or left unfilled. The Yucatan minipig mammary gland lumpectomy model shared several similarities with clinical lumpectomy, including the hardening of unrepaired and reconstructed defects, dimpling of unreconstructed defects, and a raised appearance to many of the reconstructed defects.

The surgical techniques used in these experiments resulted in the production of significant granulation tissue. Granulation tissue was observed for all surgical implantation sites, including empty voids (e.g., sites where tissue was removed but no implant was used to fill the void space). In contrast, implantation of tissue treatment products without surgical void creation resulted in little evidence of granulation tissue, as compared to the same material when implanted in a prepared void. This suggests that tissue treatment products themselves are not the main cause of granulation tissue in these experiments.

The implanted tissue treatment products were evaluated for persistence, biomechanics, biologic response, and interference with mammography. The implant characteristics were evaluated at three time points (0, 4, and 12 weeks). Implants generally persisted, as evidenced by a lack of dimpling, gross appearance, and ultrasound data. Persistence was measured by ultrasound and dimple depth. Biomechanics was evaluated by measuring the displacement of implanted tissue treatment product when placed under load (tonometry), by using BTC-2000™ (SRLI Technologies, Nashville, Tenn.) to measure the stiffness and other biomechanical properties of skin and underlying soft tissue, and, for putty implants, by rheology (tissue viscosity). Biologic response was evaluated by histology. Interference with mammography was evaluated by X-ray imaging.

Figure 2:
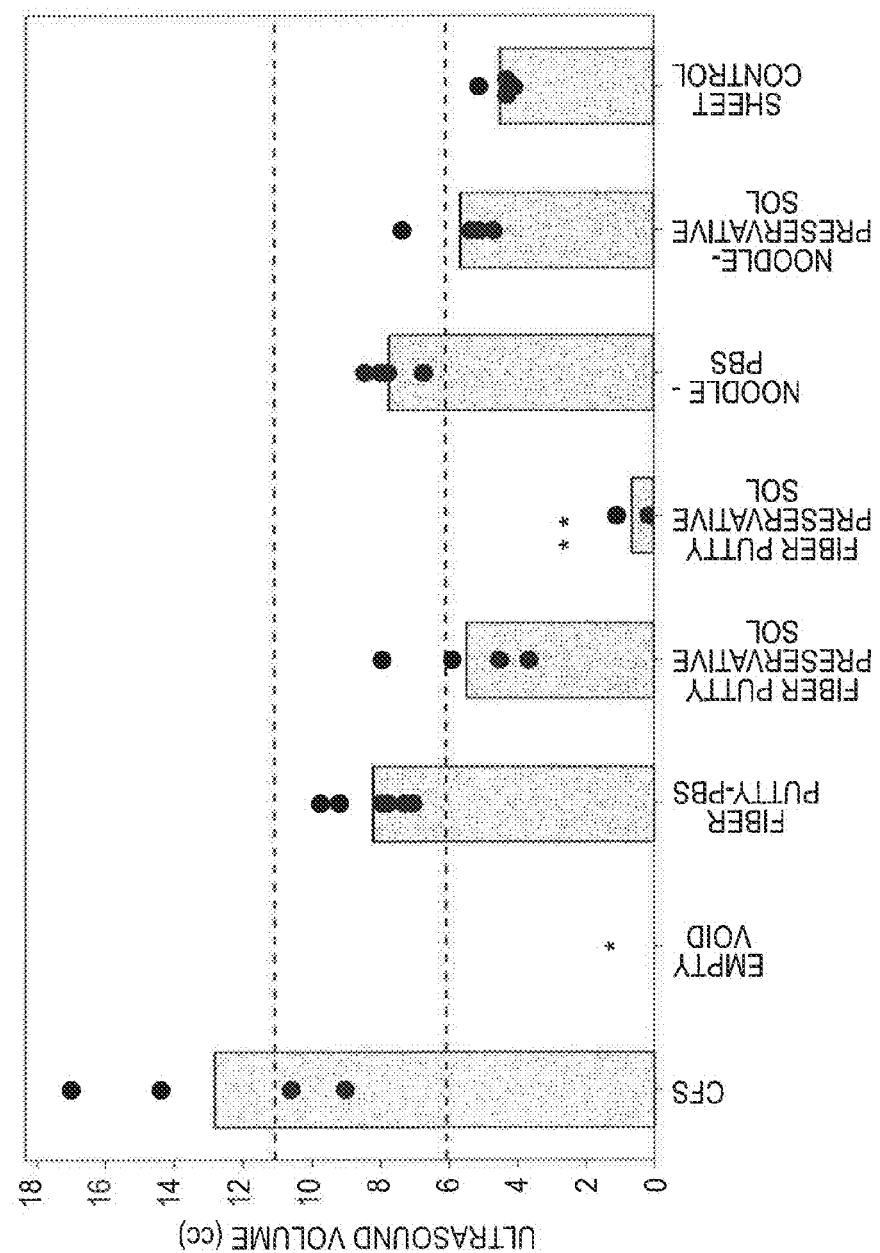
FIG. 2 shows calculated ultrasound volumes (measured in cubic centimeters) for certain tissue treatment products four weeks after implantation in a Yucatan minipig mammary gland, as described in example 2.
Figure 3:
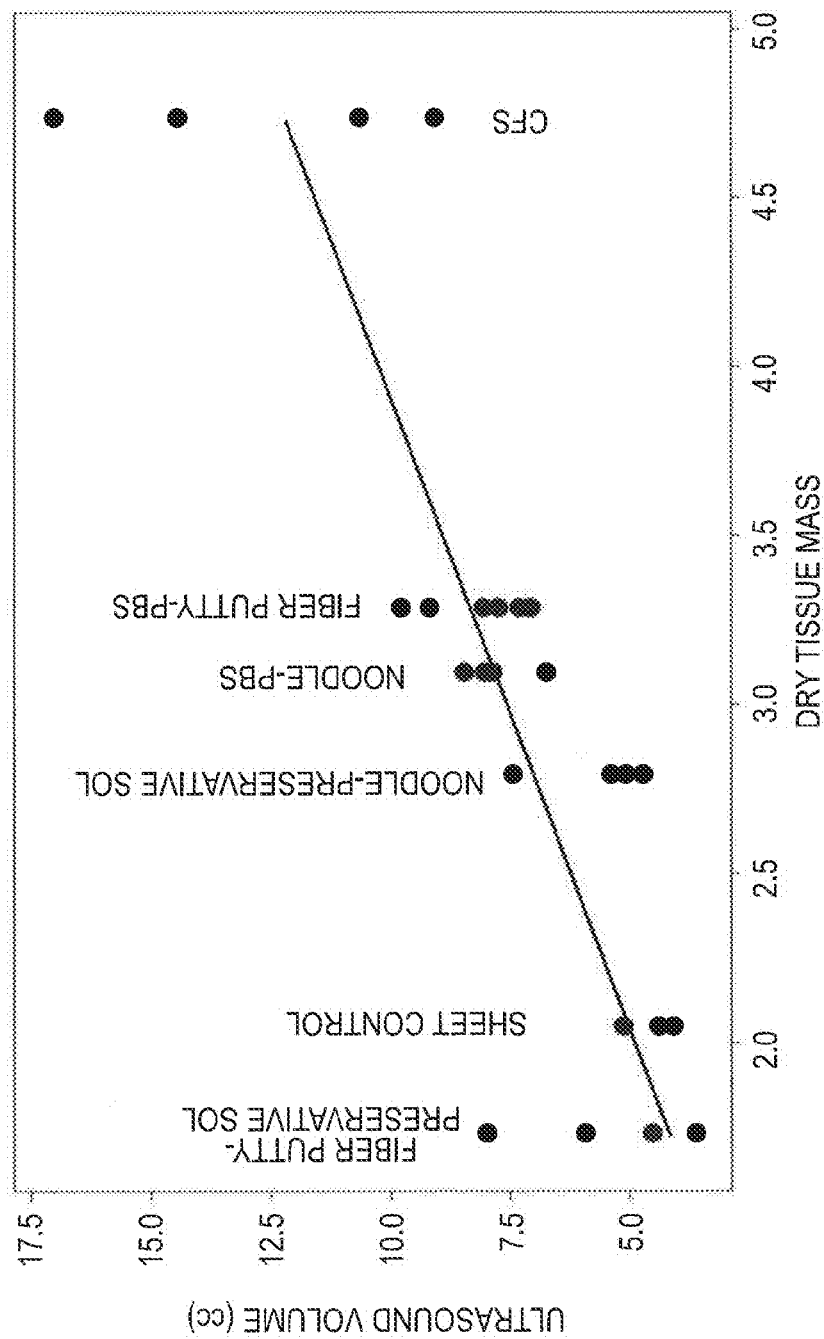
FIG. 3 is a plot of ultrasound volume (measured in cubic centimeters) against dry tissue mass for certain tissue treatment products, measured four weeks after implantation in a Yucatan minipig mammary gland, as described in example 2.
Figure 4:
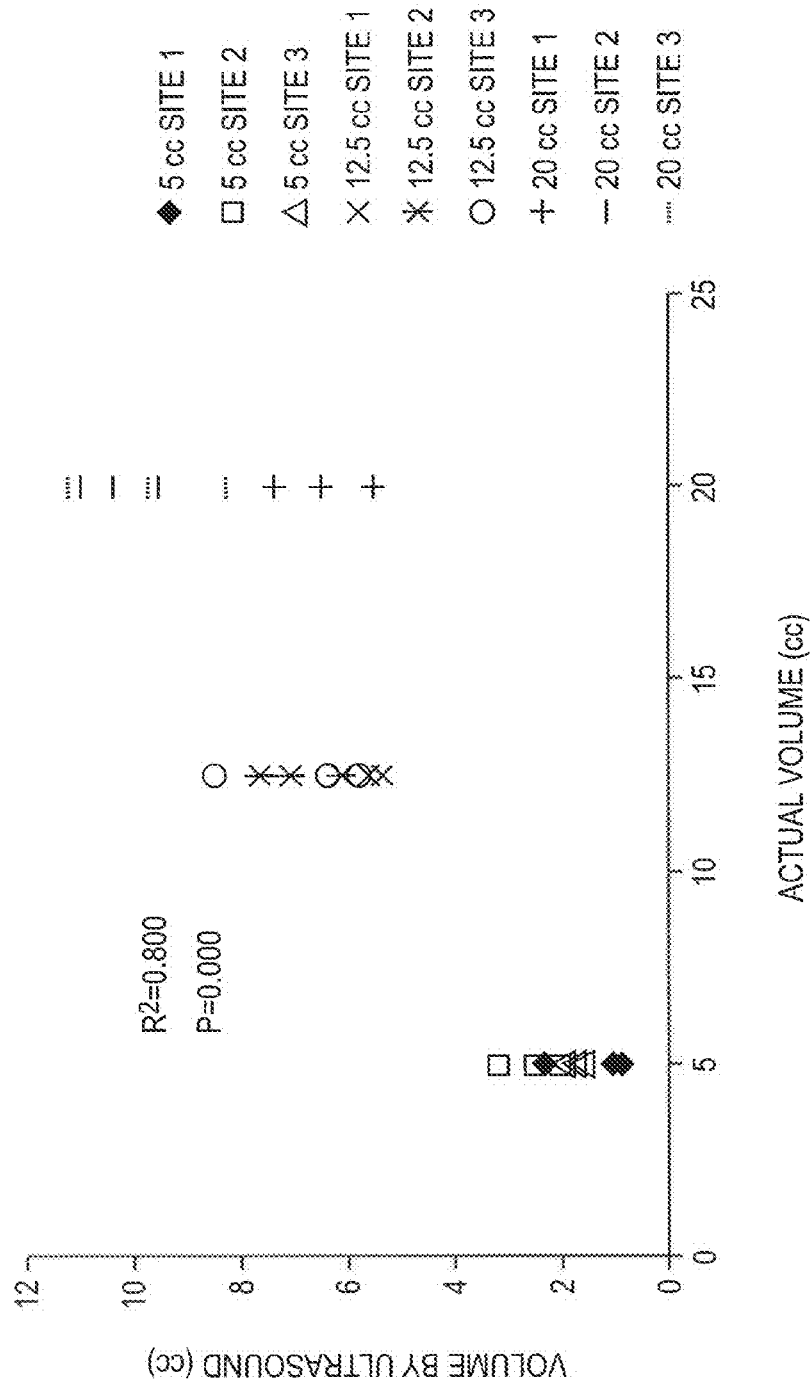
FIG. 4 is an ultrasound calibration analysis that was performed by comparing the calculated ultrasound volume immediately after implantation with the actual volumes of implanted material, as described in example 2.
Figure 16:
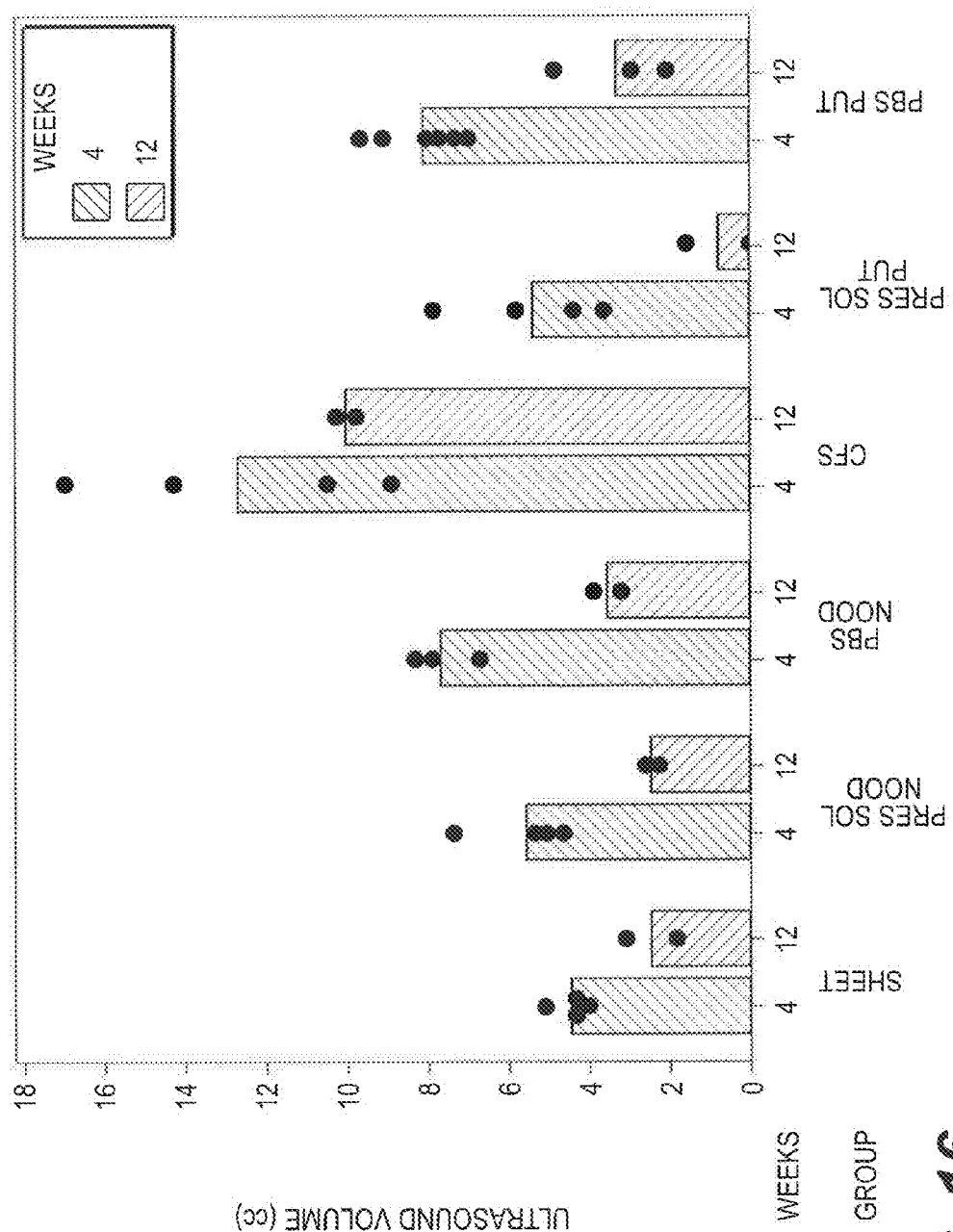
FIG. 16 compares ultrasound volume (measured in cubic centimeters) for certain tissue treatment products four weeks and twelve weeks after implantation in a Yucatan minipig mammary gland, as described in example 2.

Ultrasound was used to evaluate implant volume for the six different implanted tissue treatment products four weeks after implantation. Transverse and longitudinal images were acquired for each implant site, and volume was calculated as $\frac{4}{3}\pi abc$. FIG. 2 shows the calculated ultrasound volume for each of the different implants four weeks after implantation. FIG. 3 is a plot of ultrasound volume against dry tissue mass for the various implants, measured four weeks after implantation. Calibration of ultrasound calculations was performed by comparing the calculated ultrasound volume at time T=0 with the actual volumes of implanted material. FIG. 4. Calibration analysis illustrated that ultrasound tends to underestimate implant volume and had considerable between and within site variability. Thus, while ultrasound volume is suitable for trending purposes, it is not suitable for quantification or for detecting small differences between implants. FIG. 16 provides a comparison of ultrasound volume for the different implants at four weeks and twelve weeks after implantation. Significant volume is lost for all implants except CFS.

Figure 5:
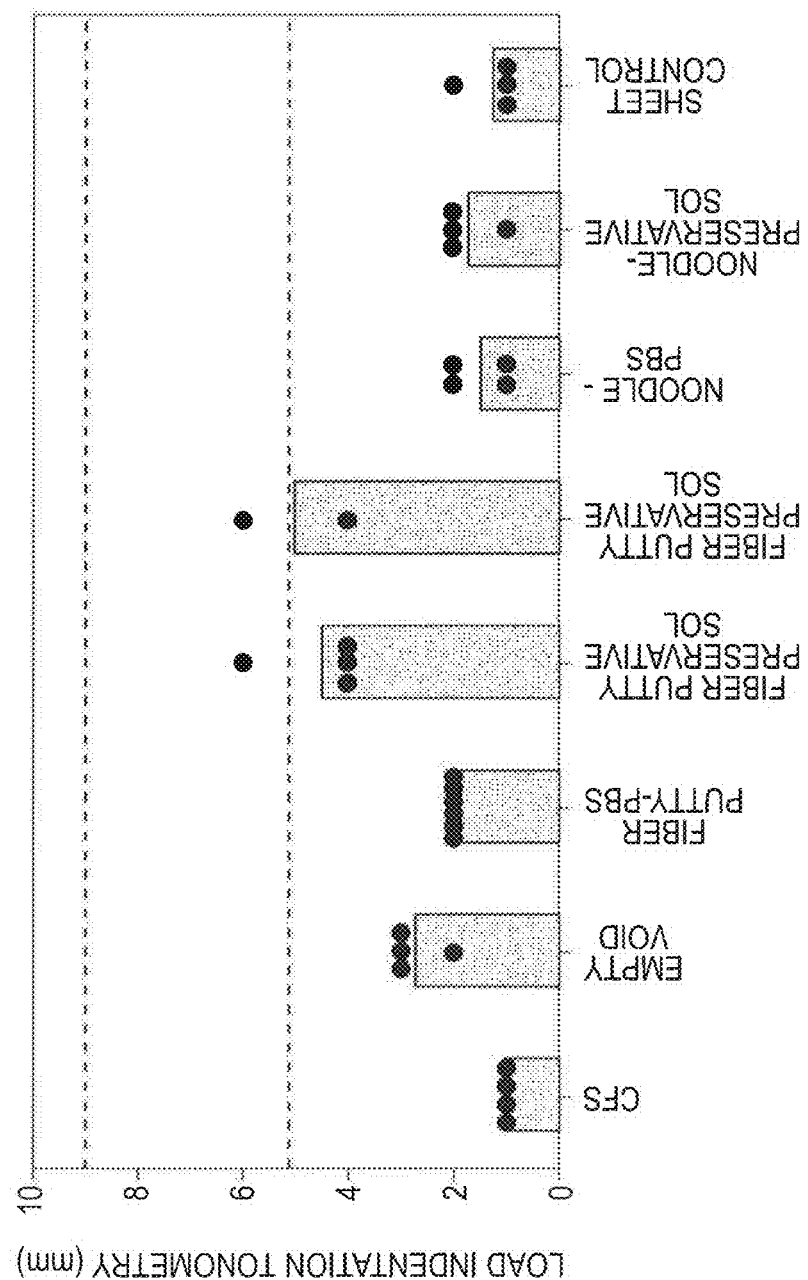
FIG. 5 is a graph showing the results of indentation tonometry assays conducted on certain tissue treatment products four weeks after implantation in a Yucatan minipig mammary gland, as described in example 2. A larger value indicates a softer (more compliant) implant site, while a lower value indicates a harder (less compliant) implant site.
Figure 6:
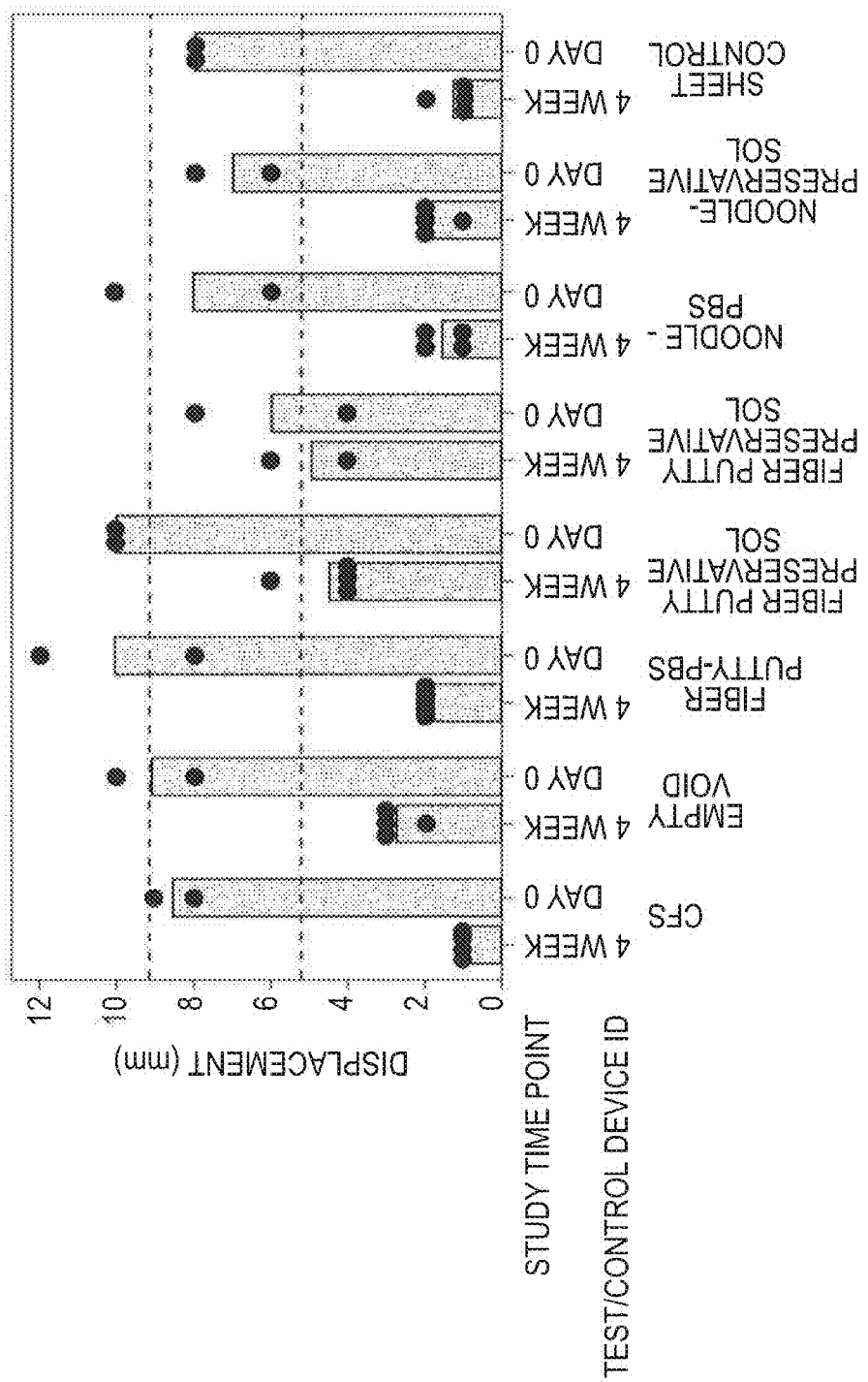
FIG. 6 compares indentation tonometry results for certain tissue treatment products that were implanted in a Yucatan minipig mammary gland, as described in example 2. Tonometry results are plotted at time T=0 and T=4 weeks.

Indentation tonometry (i.e., measuring displacement under load) was used to evaluate the biomechanical properties of implanted tissue treatment product. A 0.5 inch, 176 gram rod was placed over each implant site and the depth of rod penetration was measured. A larger value indicates a softer (more compliant) implant site, while a lower value indicates a harder (less compliant) implant site. FIG. 5 illustrates the results of indentation tonometry assays on the various implanted tissue treatment products 4 weeks after implantation. FIG. 6 compares indentation tonometry results at time T=0 and T=4 weeks for each tissue treatment product. All tissue treatment products became less compliant after 4 weeks, as measured by indentation tonometry. These quantitative results were confirmed by manual palpation. Due to implant dimpling at 12 weeks, tonometry data was inconsistent and therefore not reported except for CFS implants and putty implants in a preservative solution that did not dimple (not shown).

Figure 7:
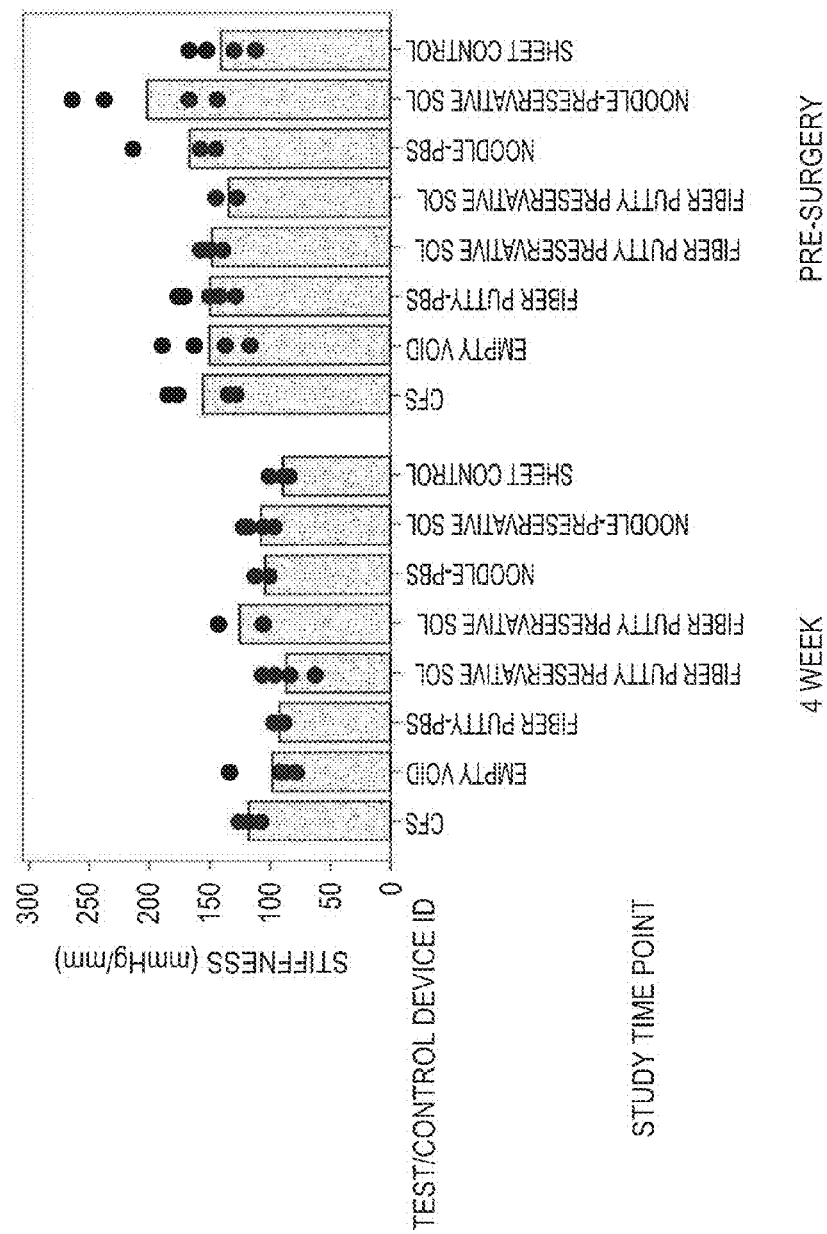
FIG. 7 is a plot of stiffness values for certain tissue treatment products that were implanted in a Yucatan minipig mammary gland, as measured by BTC-2000™ (SRLI Technologies, Nashville, Tenn.), as described in example 2.

To further evaluate the biomechanical properties of implanted tissue treatment products, BTC-2000™ (SRLI Technologies, Nashville, Tenn.) was used to measure the stiffness of tissue implants at the time of implantation and after 4 weeks. BTC-2000 can be used for quantitative and sensitive analyses of the biomechanical properties of skin and soft tissues, as well as the intact and/or disruptive characteristics of elastic materials. FIG. 7 indicates that implant stiffness decreased at 4 weeks compared to pre-surgery. This is in contrast to the increased stiffness over time observed by indentation tonometry.

Figure 8:
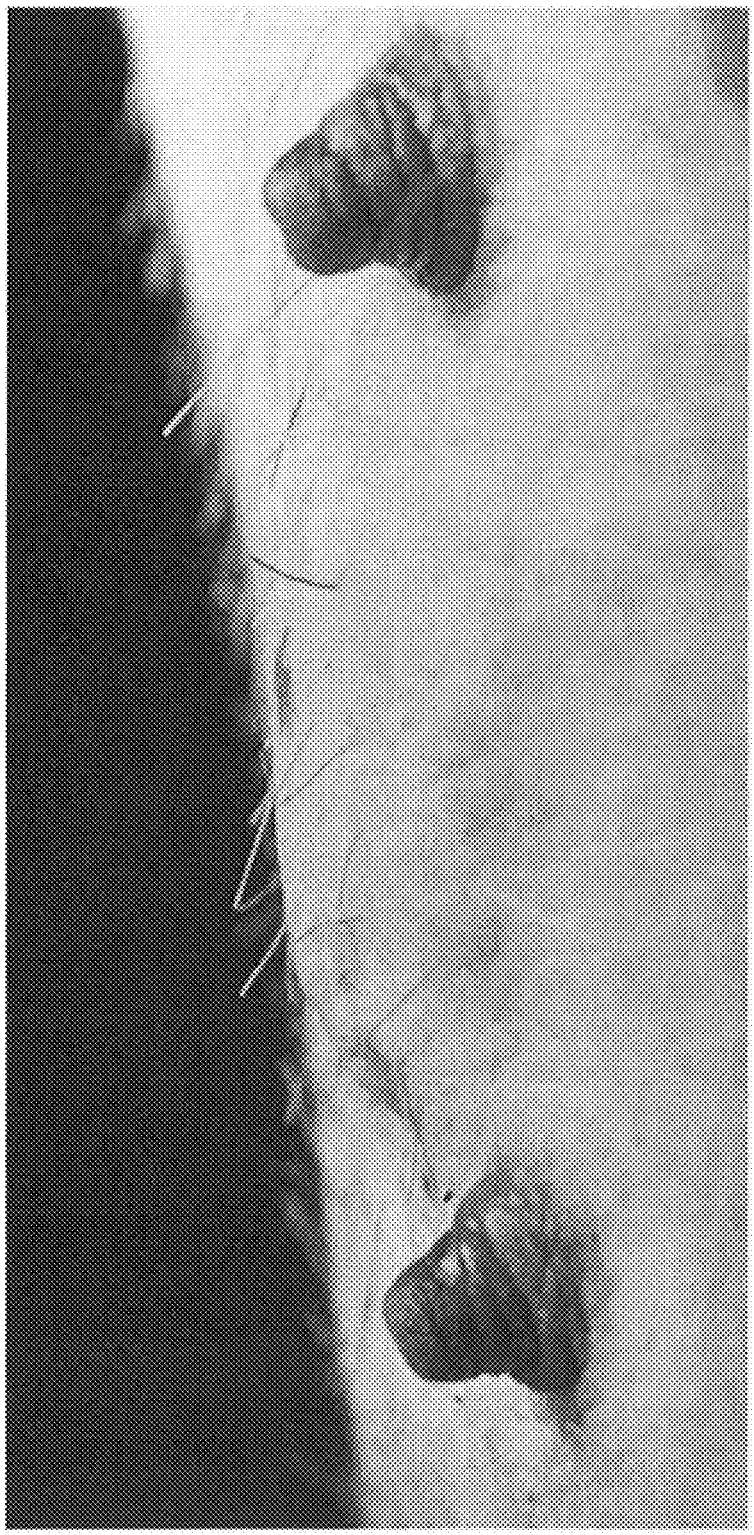
FIG. 8 is a photograph of a raised mammary gland four weeks after implantation of a representative tissue treatment product in a Yucatan minipig mammary gland, as described in example 2.
Figure 9:
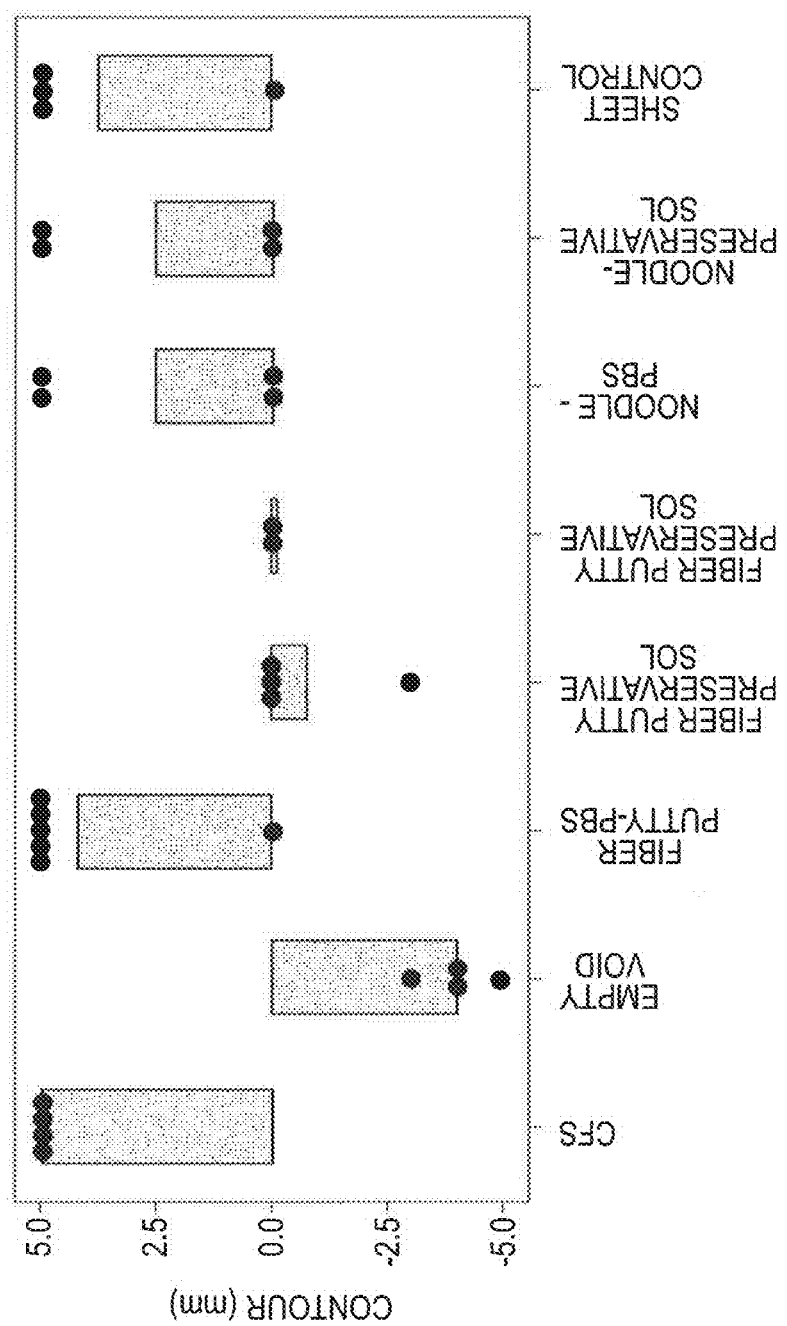
FIG. 9 is a plot of dimple depth, as measured by non-load tonometry, for certain tissue treatment products four weeks after implantation in a Yucatan minipig mammary gland, as described in example 2.
Figure 17A:
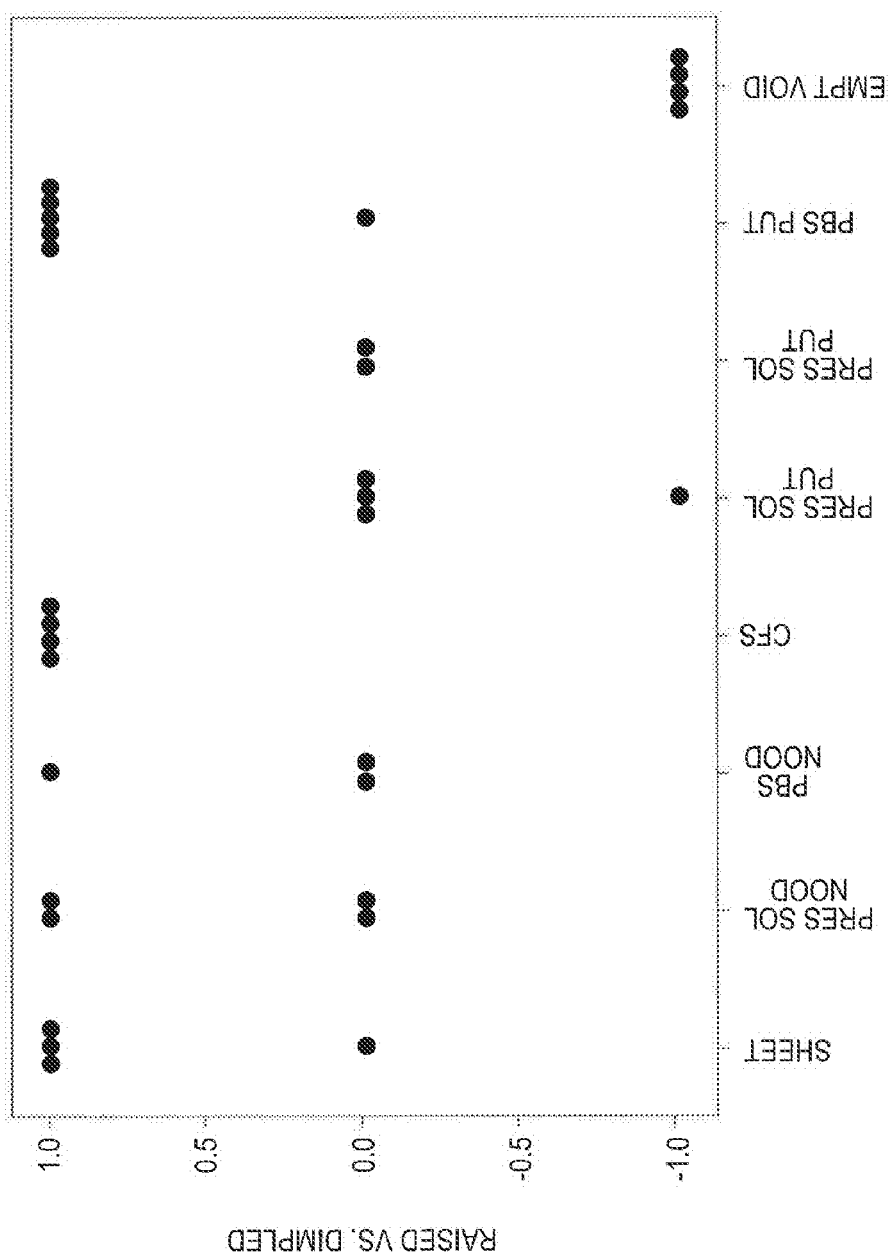
FIG. 17 is a comparison of raised or dimpled implants containing certain tissue treatment products four weeks (FIG. 17A) and twelve weeks (FIG. 17B) after implantation in a Yucatan minipig mammary gland, as described in example 2.
Figure 17B:
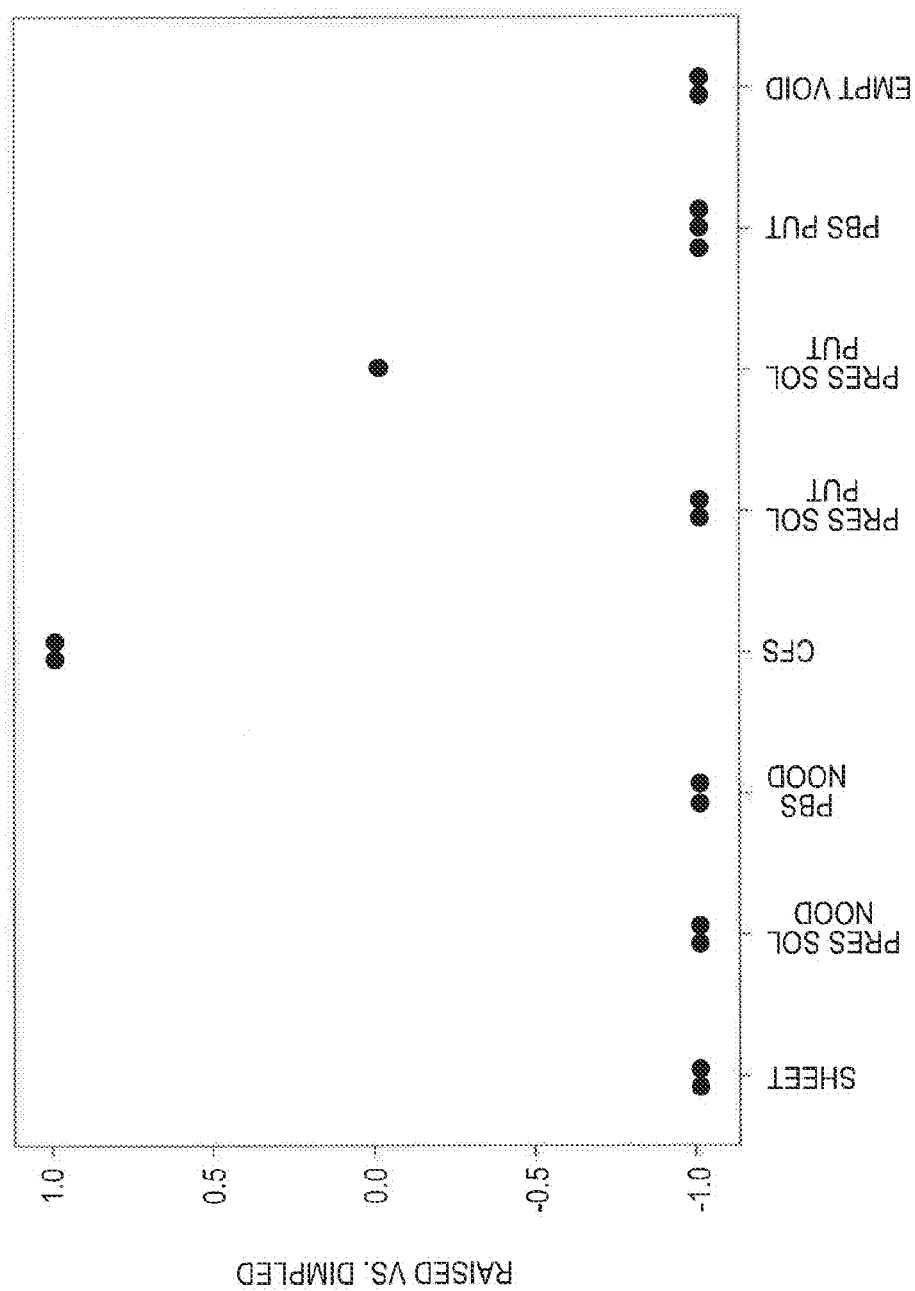

Finally, the impact of implanted tissue treatment products on tissue contour was evaluated by measuring dimple depth for sunken implant sites, as well as by photographic observation of raised implant sites. FIG. 8 is a representative example of a raised site. Such sites were estimated to be raised by 5-10 mm. Dimple depth was measured using non-load tonometry. A 176 g rod was used to measure dimple depth while the rod's weight was supported from above so that the measurement would not incorporate additional depth due to the displacement or compression of the tissue under load. FIG. 9 is a plot of dimple depth at four weeks, as measured by non-load tonometry, for the various implanted tissue treatment products, including implanted noodles. FIG. 17 is a comparison of raised or dimpled implants at 4 weeks and 12 weeks for each implant type.

Figure 10B:
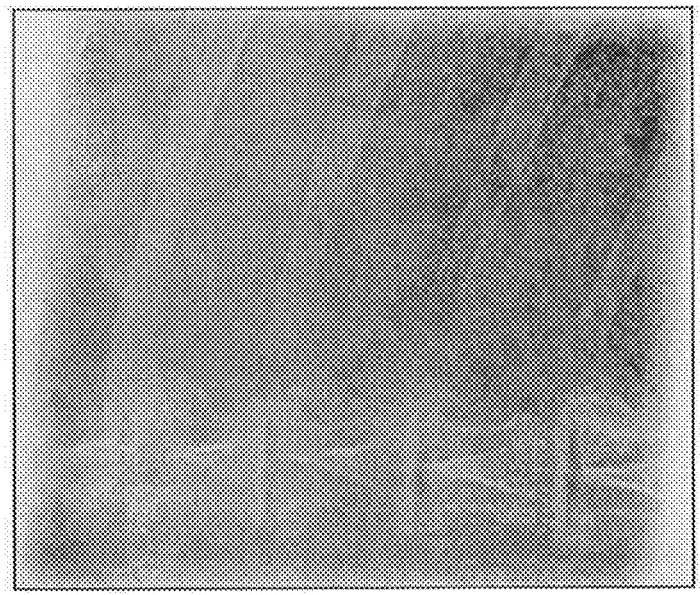
FIG. 10 shows X-ray imaging of a Yucatan minipig mammary gland before surgery (FIG. 10A) and four weeks after implantation of tissue treatment products (FIG. 10B), as described in example 2.
Figure 10A:
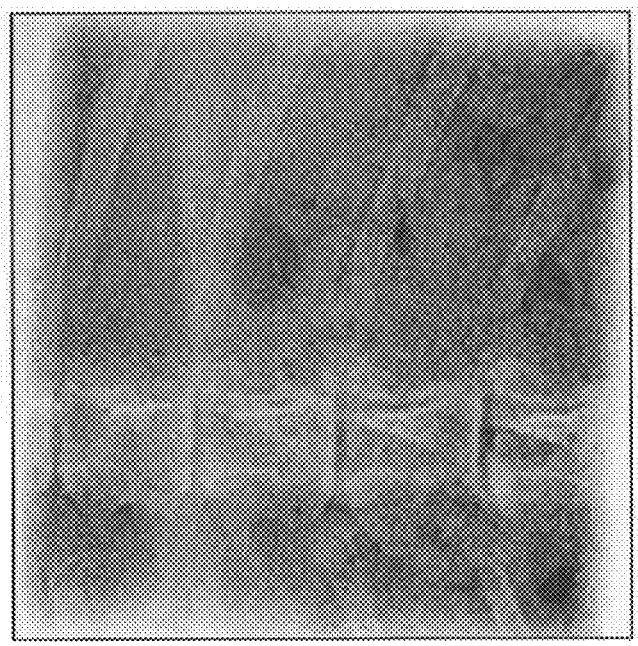

In order to evaluate the potential for implanted tissue treatment products to interfere with mammography, Yucatan minipig mammary glands were imaged by 70 KV X-ray before surgery and 4 weeks after implantation of a noodle tissue treatment product (FIGS. 10A and B, respectively). No differences in tissue density between implant site and surrounding tissue were detected by X-ray following noodle implantation. However, the 70 KV energy used in this experiment was higher than the 15-52 KV normally used in mammography, which may have prevented detection of differences in tissue density.

To evaluate the biologic response to implanted tissue treatment products, including implanted noodles, gross observation was recorded and histology was performed four weeks and twelve weeks after implantation.

Figure 11:
FIG. 11 is a photograph showing the gross anatomical structure of a high aspect ratio tissue treatment product (in PBS) four weeks after implantation in a Yucatan minipig mammary gland, as described in example 2.
Figure 12:
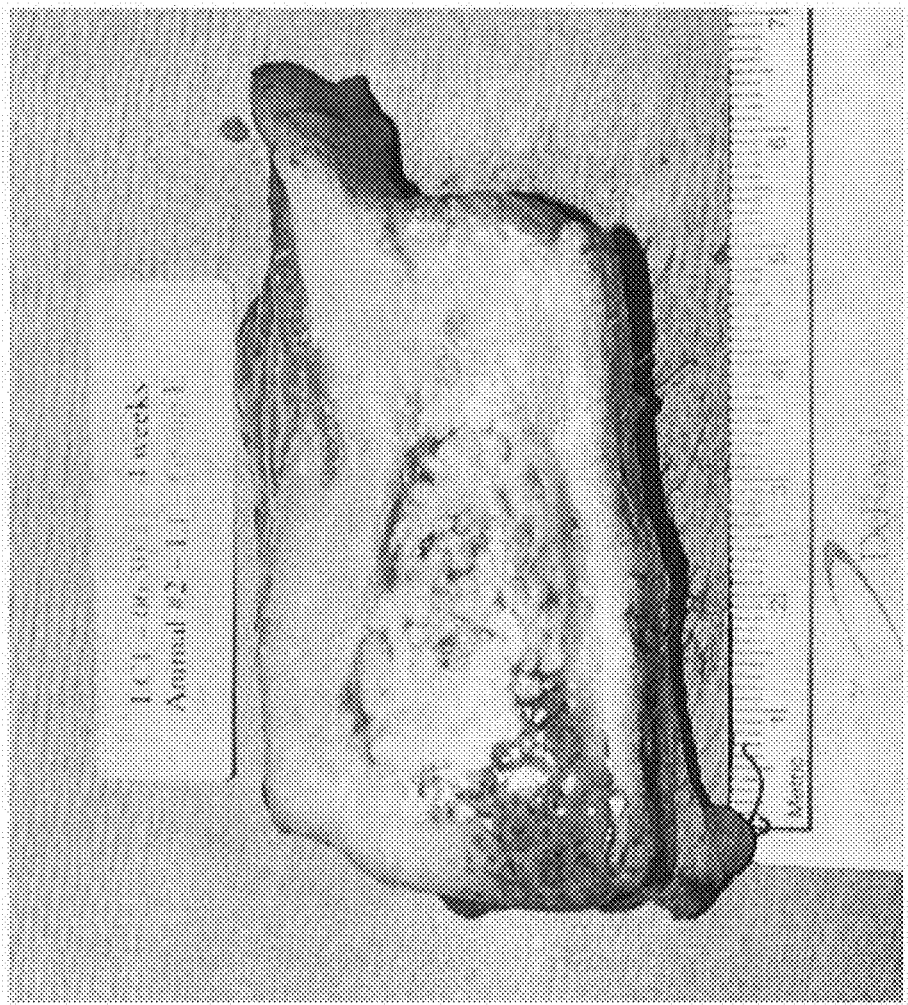
FIG. 12 is a photograph showing the gross anatomical structure of a high aspect ratio tissue treatment product (in a preservative solution) four weeks after implantation in a Yucatan minipig mammary gland, as described in example 2.
Figure 13:
FIG. 13 shows H&E staining of a high aspect ratio tissue treatment product (in PBS) four weeks after implantation in a Yucatan minipig mammary gland, as described in example 2.
Figure 14:
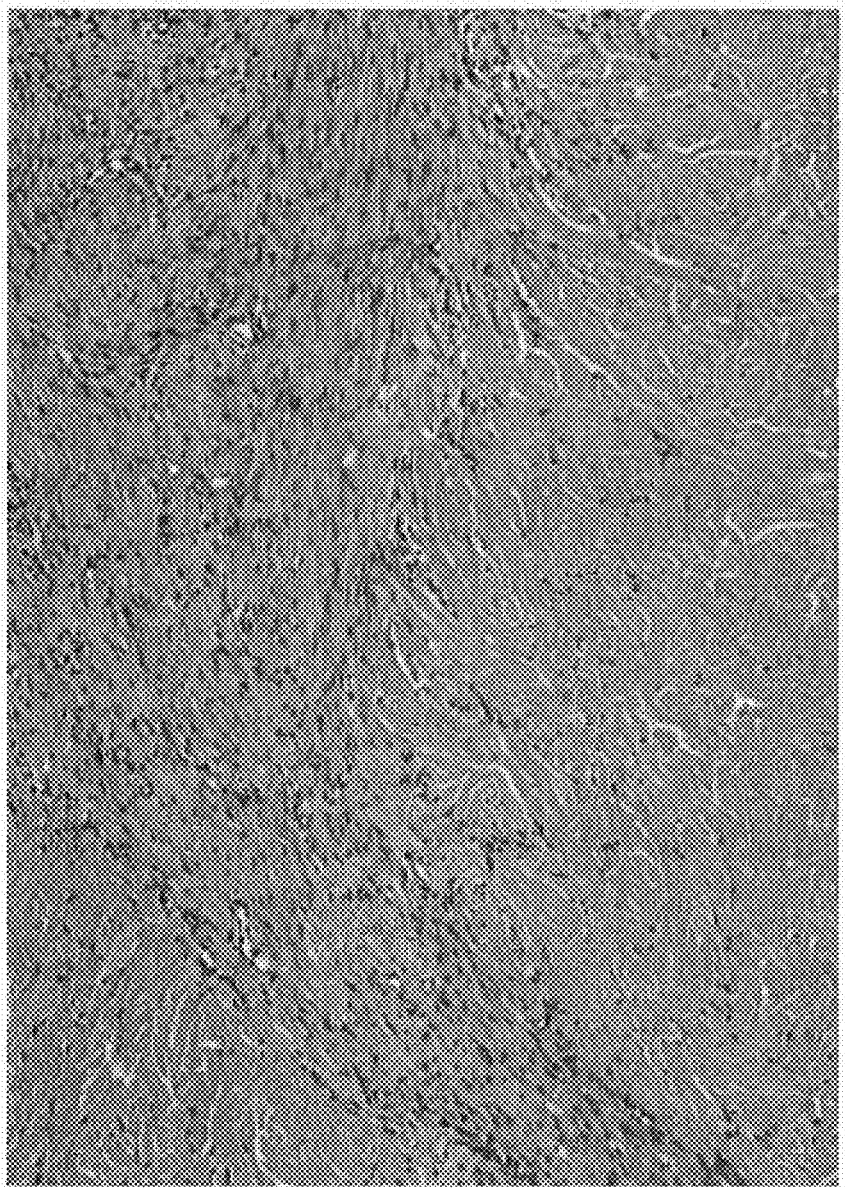
FIG. 14 shows H&E staining of a high aspect ratio tissue treatment product (in a preservative solution) four weeks after implantation in a Yucatan minipig mammary gland, as described in example 2.
Figure 15A:
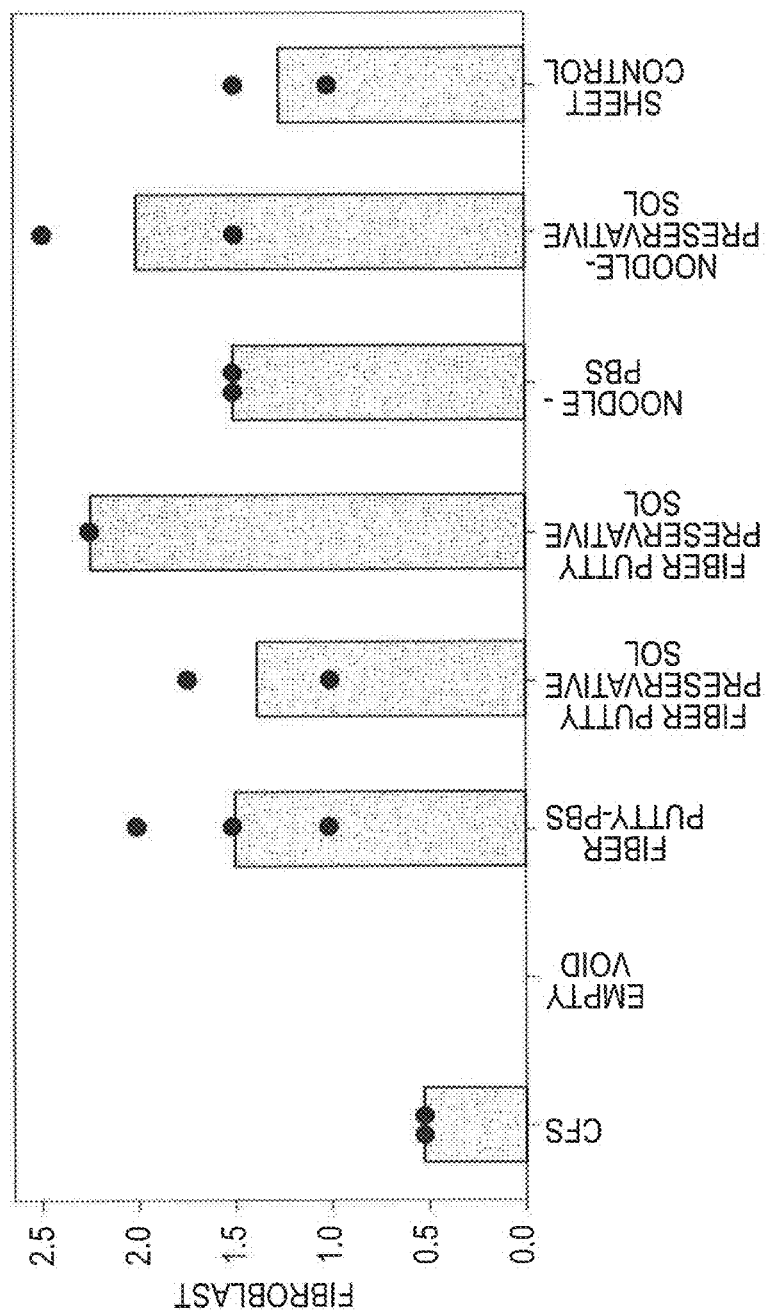
FIG. 15 shows histology scoring of H&E stained tissue treatment products four weeks after implantation in a Yucatan a minipig mammary gland, as described in example 2. Tissue treatment products were scored for fibroblasts (FIG. 15A), revascularization (FIG. 15B), and inflammation (FIG. 15C).
Figure 15B:
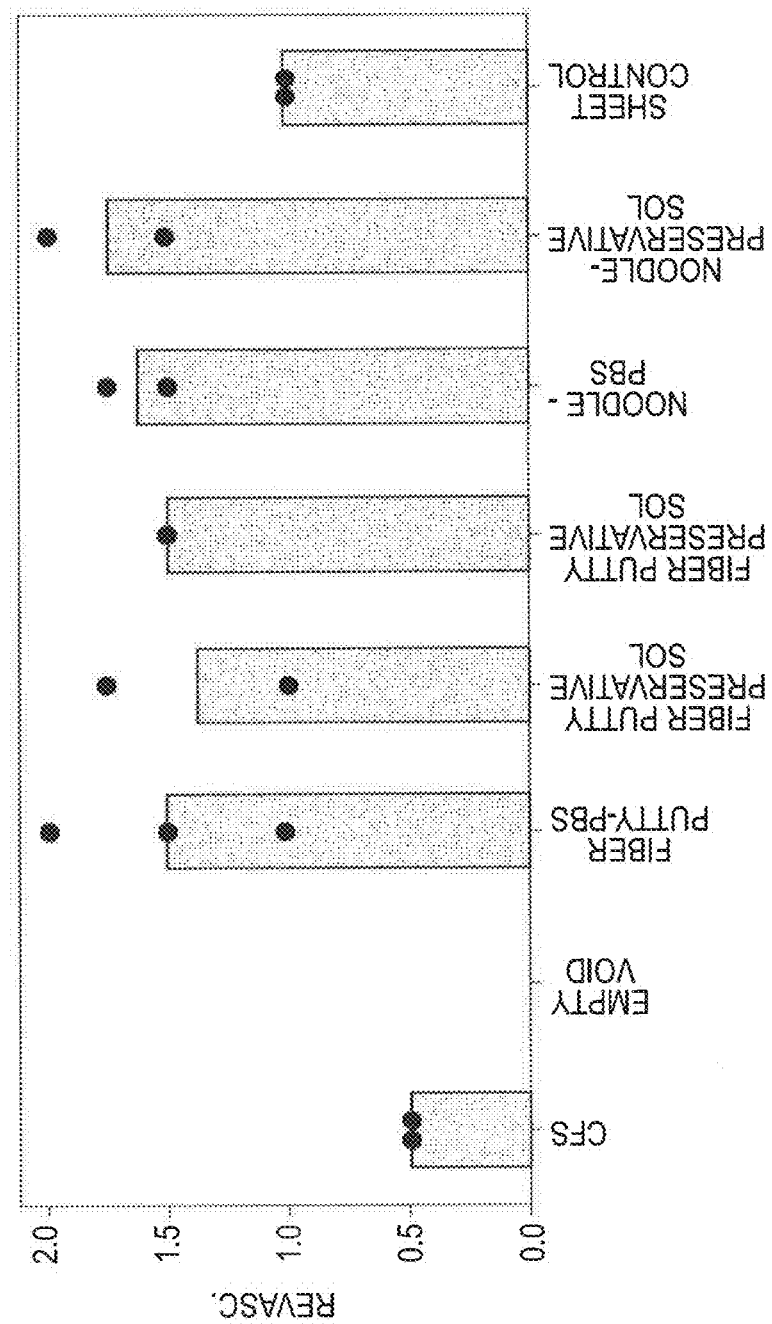
Figure 15C:
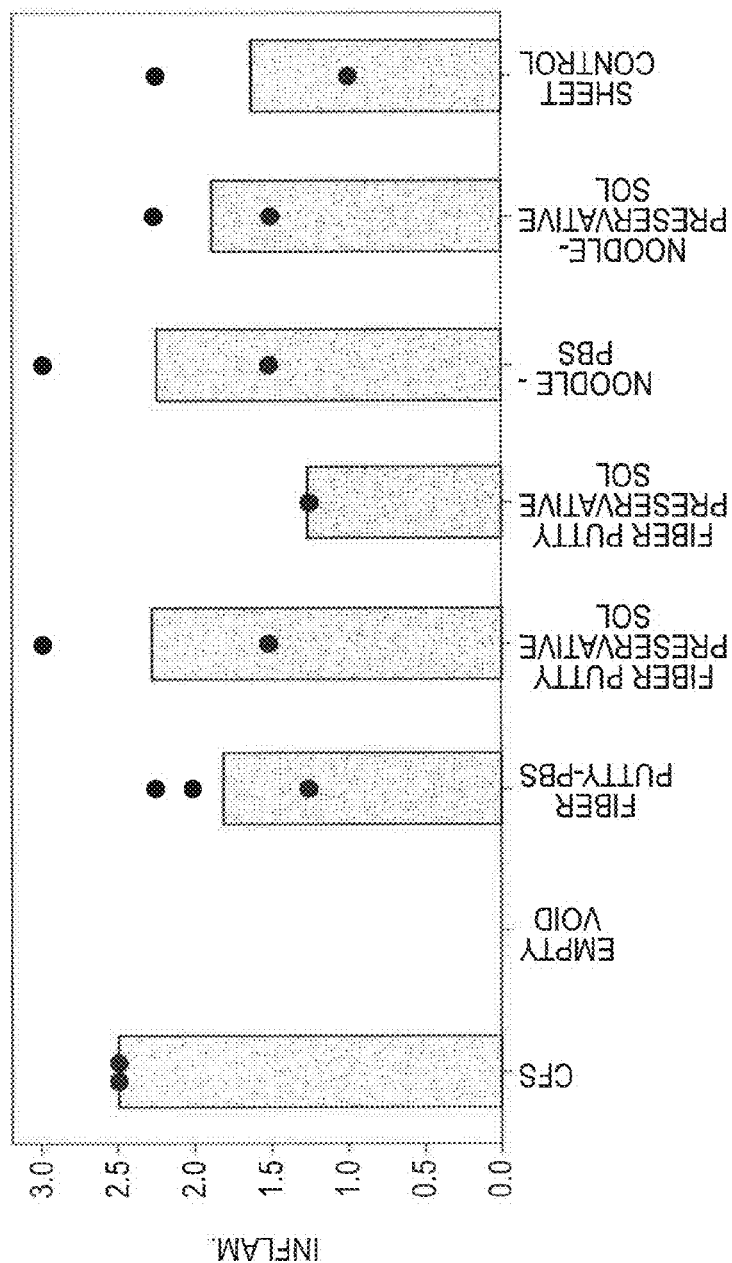

After four weeks, gross observations were recorded photographically for implanted noodles in PBS and implanted noodles in a preservative solution. See FIGS. 11 and 12, respectively. Histology was performed with hematoxylin and eosin (H&E) staining to evaluate fibroblast repopulation, inflammation, and revascularization. FIGS. 13 and 14 show H&E staining for implanted noodles in PBS and in a preservative solution, respectively. FIG. 15 shows histology scoring of H&E stained tissue for fibroblasts (FIG. 15A), revascularization (FIG. 15B), and inflammation (FIG. 15C). Histology scoring was conducted on stained samples from various tissue treatment products, including implanted noodles, four weeks after plantation.

Figure 18:
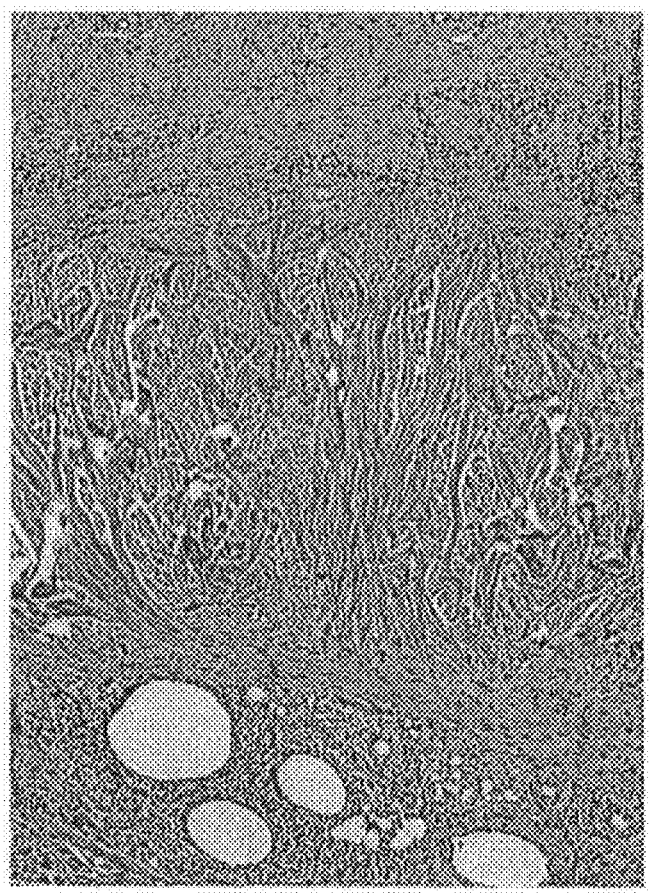
FIG. 18 shows H&E staining of a high aspect ratio tissue treatment product (in PBS) twelve weeks after implantation in a Yucatan minipig mammary gland, as described in example 2.
Figure 19:
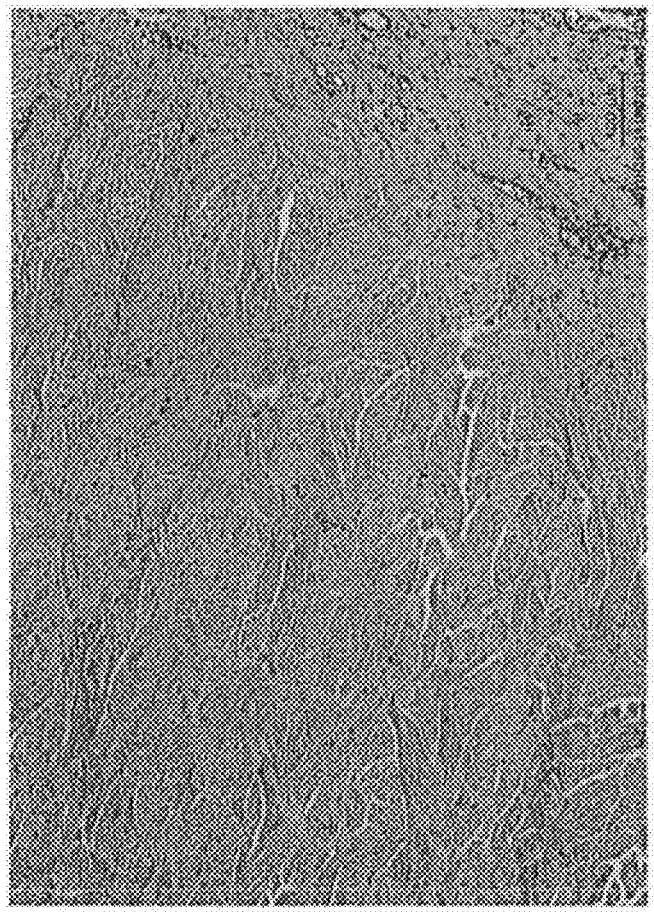
FIG. 19 shows H&E staining of a high aspect ratio tissue treatment product (in a preservative solution) twelve weeks after implantation in a Yucatan minipig mammary gland, as described in example 2.
Figure 20A:
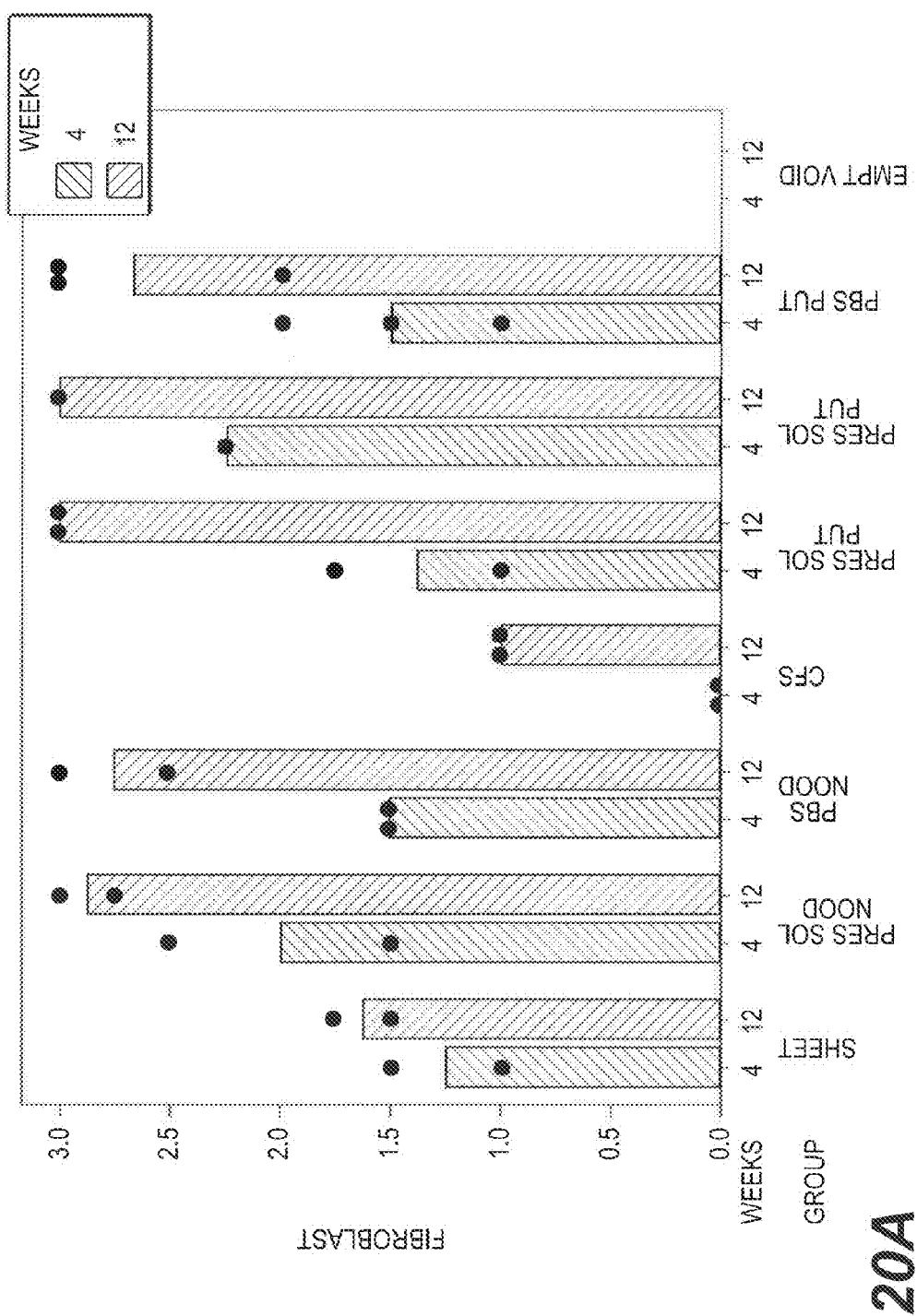
FIG. 20 shows histology scoring of H&E stained tissue treatment products four weeks and twelve weeks after implantation in a Yucatan minipig mammary gland, as described in example 2. Tissue treatment products were scored for fibroblasts (FIG. 20A), revascularization (FIG. 20B), and inflammation (FIG. 20C).
Figure 20B:
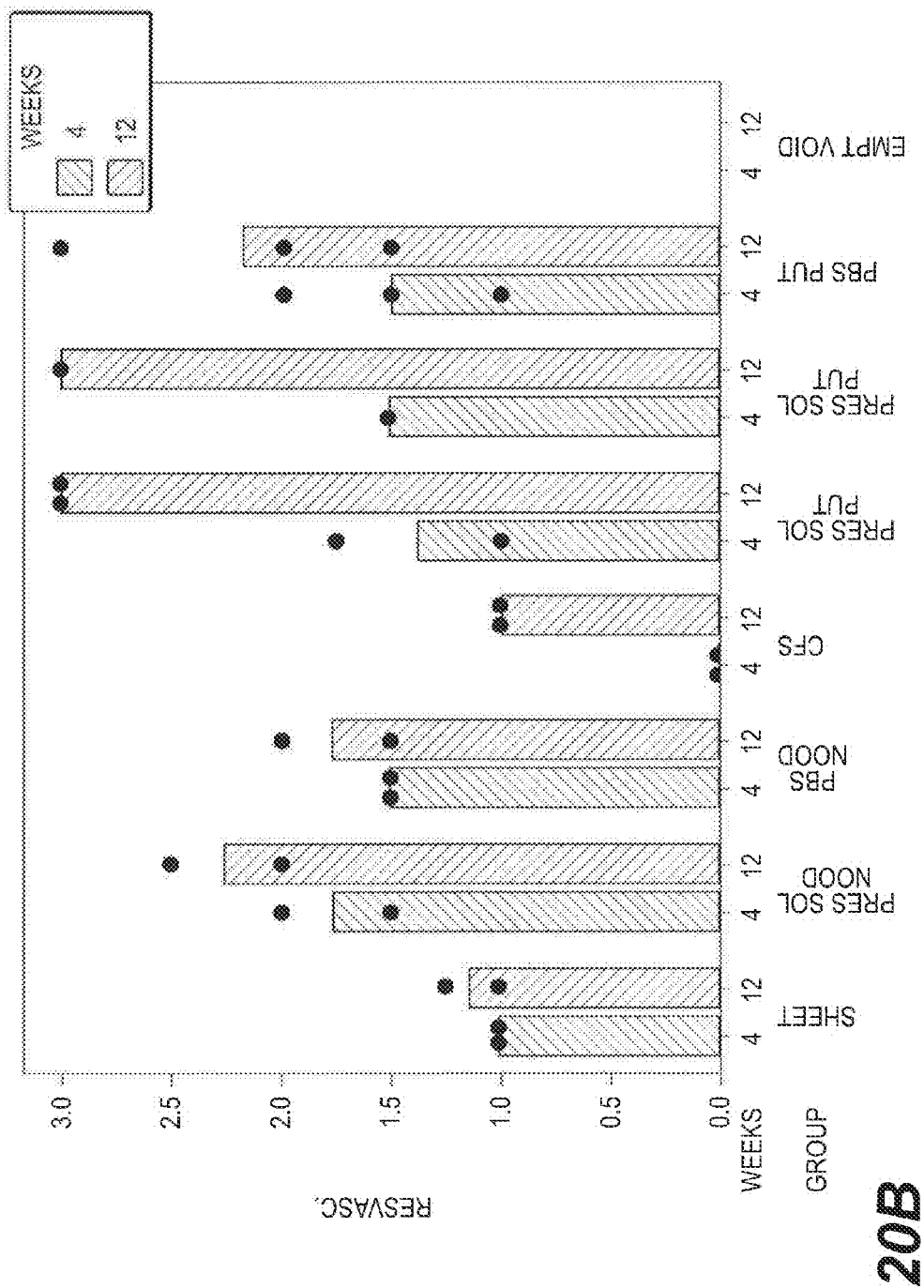
Figure 20C:
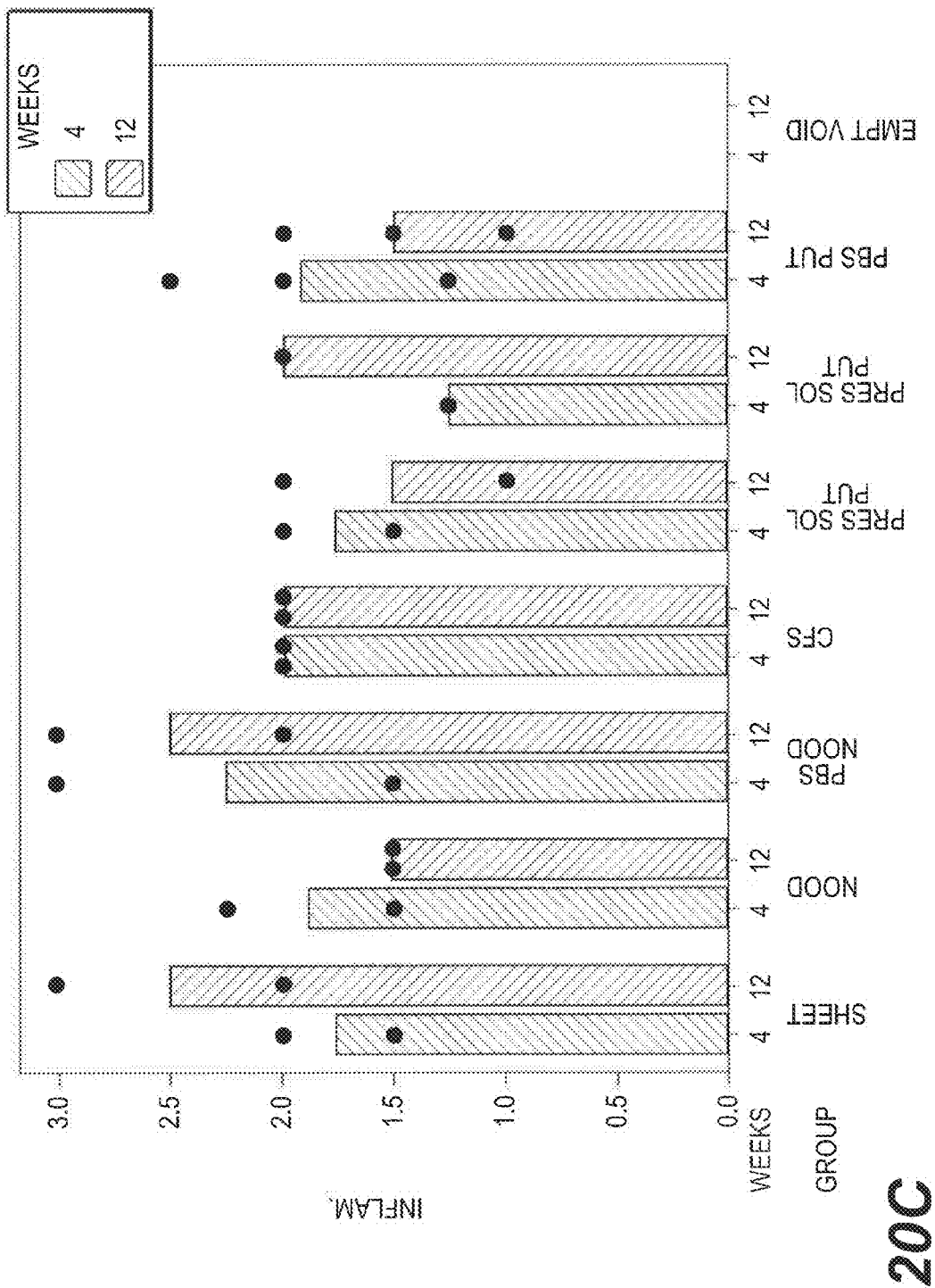

After twelve weeks, implanted noodles in PBS demonstrated significant fibroblast repopulation and mild revascularization. There was also a moderate inflammatory response, as evidenced by the presence of lymphocytes, macrophages, and giant cells. Dense connective tissue was observed between the implanted noodles. FIG. 18. For noodles in a preservation solution, significant fibroblast repopulation and moderate revascularization was again observed. A mild inflammatory response was observed. Dense connective tissue was observed between the implanted noodles. FIG. 19. FIG. 20 shows histology scoring of H&E stained tissue for fibroblasts (FIG. 20A), revascularization (FIG. 20B), and inflammation (FIG. 20C) at four weeks and twelve weeks after implantation.

The preceding examples are intended to illustrate and in no way limit the present disclosure. Other embodiments of the disclosed devices and methods will be apparent to those skilled in the art from consideration of the specification and practice of the devices and methods disclosed herein.

What is claimed is:

1. A method for treating a surgical site in a breast after a lumpectomy procedure, comprising selecting a surgical site; removing native breast tissue; selecting an amount of a tissue treatment product sufficient to replace the native tissue excised from the surgical site; and implanting the tissue treatment product into the surgical site, wherein the tissue treatment product comprises:
    a collection of loosely arranged elongated elements lacking an organized tertiary structure, each elongated element comprising a tissue matrix that has been at least partially decellularized, and wherein each elongated element has a flexible three-dimensional structure comprising a length dimension, a width dimension, and a height dimension, and wherein one dimension is substantially larger than the other two dimensions, wherein the collection of loosely arranged elongated elements are implanted in contact with surrounding tissue to allow ingrowth of cells.

2. The method of claim 1, wherein implanting the tissue treatment product preserves the look and feel of breast tissue prior to surgical removal of native tissue, while providing a structural scaffold in which native cells and vasculature can migrate and proliferate.

3. The method of claim 2, wherein the implanted tissue treatment product promotes or enhances breast tissue repair, regeneration, or treatment by providing a scaffold for the regeneration of native breast tissue and by reducing the volume of fibrosis formed at the site of surgical intervention, as compared to fibrosis formation in the absence of an implanted tissue treatment product.

4. A method of treatment, comprising implanting a tissue treatment product into a tissue in need of repair, regeneration, healing, treatment, or alteration, wherein the tissue treatment product comprises:
a collection of loosely arranged elongated elements lacking an organized tertiary structure, each elongated element comprising a tissue matrix that has been at least partially decellularized, and
wherein each elongated element has a flexible three-dimensional structure comprising a length dimension, a width dimension, and a height dimension, and wherein one dimension is substantially larger than the other two dimensions, wherein the collection of loosely arranged elongated elements are implanted in contact with surrounding tissue to allow ingrowth of cells.

5. The method of claim 4, wherein the tissue treatment product conforms to the anatomic shape of an implant site, resists migrating away from the implant site after implantation, and allows for the continued passage of fluid at the site of implantation.

6. The method of claim 5, wherein the implanted tissue treatment product provides a structural scaffold in which native cells and vasculature can migrate and proliferate.

7. The method of claim 6, wherein the tissue treatment product promotes or enhances tissue repair, regeneration, healing, treatment, or alteration.

8. The method of claim 4, wherein the tissue treatment product is implanted for cosmetic purposes.

9. The method of claim 8, wherein the tissue treatment product is used in combination with a breast implant.

10. The method of claim 4, wherein the tissue treatment product is implanted following the removal of native tissue.

11. The method of claim 10, wherein the tissue being removed is a tumor.

12. The method of claim 11, wherein the tumor is a breast tumor.

13. The method of claim 10, wherein implanting a tissue treatment product preserves the approximate look or feel of the native tissue after implantation, as compared to the look or feel in the absence of an implanted tissue treatment product.

14. The method of claim 4, wherein the tissue treatment product is implanted following surgical separation of native tissues.

15. The method of claim 14, wherein implanting the tissue treatment product leads to faster healing of the separated native tissues, as compared to healing in the absence of an implanted tissue treatment product.

16. The method of claim 4, wherein the tissue treatment product is implanted in a wound or other void space that occurs through injury or disease.

17. The method of claim 16, wherein implanting the tissue treatment product leads to faster healing of the wound or void space, as compared to healing in the absence of an implanted tissue treatment product.

18. The method of claim 4, wherein the tissue treatment product comprises a collection of elements that have a high aspect ratio.

19. The method of claim 18, wherein the high aspect ratio elements in the tissue treatment product have one dimension that is at least about five times as large as the other two dimensions.

20. The method of claim 18, wherein the high aspect ratio elements in the tissue treatment product have one dimension that is at least about ten times as large as the other two dimensions.

21. The method of claim 18, wherein the high aspect ratio elements in the tissue treatment product have one dimension that is at least about 100 times as large as the other two dimensions.

22. The method of claim 4, wherein the tissue treatment product comprises a partially or fully decellularized tissue matrix from at least one of human, non-human primate, pig, cow, horse, goat, sheep, dog, cat, rabbit, guinea pig, gerbil, hamster, rat, and mouse tissue.

23. The method of claim 4, wherein the tissue treatment product comprises the partially or fully decellularized tissue matrix from at least one of bone, skin, dermis, intestine, vascular, urinary bladder, tendon, ligament, muscle, fascia, neurologic tissue, vessel, liver, heart, lung, kidney, or cartilage tissue.

24. The method of claim 4, wherein the tissue treatment product further comprises one or more viable and histocompatible cells.

25. The method of claim 4, wherein the tissue treatment product further comprises at least one additional factor selected from an anti-inflammatory agent, an analgesic, a cell growth factor, an angiogenic factor, a differentiation factor, a cytokine, a hormone, and a chemokine.

26. The method of claim 4, wherein the tissue treatment product substantially lacks all bioburden.

27. The method of claim 4, wherein the tissue treatment product is injected through a syringe.

* * * * *